US009519021B2

(12) United States Patent
Gilbert

(10) Patent No.: US 9,519,021 B2
(45) Date of Patent: Dec. 13, 2016

(54) SYSTEMS AND METHODS FOR DETECTING ABNORMALITIES WITHIN A CIRCUIT OF AN ELECTROSURGICAL GENERATOR

(71) Applicant: COVIDIEN LP, Mansfield, MA (US)

(72) Inventor: James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 135 days.

(21) Appl. No.: 14/147,294

(22) Filed: Jan. 3, 2014

(65) Prior Publication Data
US 2014/0253140 A1 Sep. 11, 2014

Related U.S. Application Data

(60) Provisional application No. 61/776,523, filed on Mar. 11, 2013.

(51) Int. Cl.
*G01R 31/28* (2006.01)
*A61B 18/12* (2006.01)
*A61B 18/14* (2006.01)

(52) U.S. Cl.
CPC ......... *G01R 31/282* (2013.01); *A61B 18/1206* (2013.01); *A61B 18/1233* (2013.01); *A61B 18/1402* (2013.01); *A61B 18/1445* (2013.01)

(58) Field of Classification Search
CPC ........ G01R 31/28; G01R 31/282; G01R 31/02
USPC ................ 324/765, 73.1, 512–536, 415–424
See application file for complete search history.

(56) References Cited

U.S. PATENT DOCUMENTS

| | | | |
|---|---|---|---|
| 4,658,815 A | 4/1987 | Farin et al. | |
| 4,739,759 A | 4/1988 | Rexroth et al. | |
| 5,173,847 A * | 12/1992 | Suzuki | H02M 3/33592 363/21.14 |
| 5,768,124 A * | 6/1998 | Stothers et al. | 700/38 |
| 6,009,074 A * | 12/1999 | Kim et al. | 370/209 |
| 6,088,581 A * | 7/2000 | Bickley et al. | 455/131 |
| 6,289,487 B1 * | 9/2001 | Hessel et al. | 714/795 |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

Search Report issued on May 26, 2014 in corresponding European patent application No. 14158041.5.

(Continued)

*Primary Examiner* — Jermele M Hollington
*Assistant Examiner* — Zannatul Ferdous

(57) ABSTRACT

An electrosurgical generator includes primary and test sources. The primary source supplies a primary signal and the test source supplies a test signal. The electrosurgical generator includes an output circuit and an abnormality detection circuit. The output circuit is electrically coupled to the primary and test sources. The output circuit receives the primary and test signals from the primary and test sources, respectively. The output circuit is electrically coupled to a load to supply the primary signal thereto. The abnormality detection circuit is electrically coupled to the output circuit to detect an abnormality therein as a function of the test signal. The abnormality detection circuit can also determine a location of the abnormality within the output circuit.

20 Claims, 13 Drawing Sheets

(56) References Cited

U.S. PATENT DOCUMENTS

| | | | |
|---|---|---|---|
| 6,577,138 B2* | 6/2003 | Zuercher et al. | 324/536 |
| 6,830,569 B2 | 12/2004 | Thompson et al. | |
| 7,218,125 B2* | 5/2007 | Fitzgerald et al. | 324/715 |
| 7,301,254 B1* | 11/2007 | Lal | G21H 1/02 |
| | | | 310/309 |
| 7,353,068 B2 | 4/2008 | Tanaka et al. | |
| 7,400,995 B2* | 7/2008 | Mattes et al. | 702/118 |
| D574,323 S | 8/2008 | Waaler | |
| 7,674,261 B2 | 3/2010 | Garito et al. | |
| 8,506,565 B2 | 8/2013 | DeCarlo | |
| 2004/0164744 A1* | 8/2004 | Koga et al. | 324/537 |
| 2011/0087213 A1 | 4/2011 | Messerly et al. | |
| 2011/0301772 A1* | 12/2011 | Zuercher et al. | 700/293 |
| 2012/0265196 A1 | 10/2012 | Turner et al. | |
| 2013/0035679 A1 | 2/2013 | Orszulak | |
| 2013/0053840 A1 | 2/2013 | Krapohl et al. | |
| 2013/0066311 A1 | 3/2013 | Smith et al. | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079673 A1 | 3/2013 | Stein et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0345696 A1 | 12/2013 | Behnke, II et al. | |
| 2014/0002056 A1 | 1/2014 | Moul et al. | |
| 2014/0015535 A1 | 1/2014 | Lopez | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2510895 A1 | 10/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 2486343 A | 6/2012 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 97/11648 A2 | 4/1997 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |
| WO | 2008/053532 A1 | 5/2008 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation—'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51:(1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 13/943,518 dated Jul. 16, 2013 inventor: Orszulak et al.
U.S. Appl. No. 14/069,534 dated Nov. 1, 2013 inventor: Digmann.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/183,196 dated Feb. 18, 2014 inventor: Krapohl.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/192,112 dated Feb. 27, 2014 inventor: Weinberg.
U.S. Appl. No. 14/255,051 dated Apr. 17, 2014 inventor: Coulson.

\* cited by examiner

SYSTEMS AND METHODS FOR DETECTING ABNORMALITIES WITHIN A CIRCUIT OF AN ELECTROSURGICAL GENERATOR

CROSS REFERENCE TO RELATED APPLICATION

The present application claims the benefit of and priority to U.S. Provisional Application Ser. No. 61/776,523, filed on Mar. 11, 2013, the entire contents of which are incorporated herein by reference.

BACKGROUND

Technical Field

The present disclosure relates to electrosurgery. More particularly, the present disclosure relates to systems and methods for detecting an abnormality within a circuit of an electrosurgical generator.

Description of Related Art

Electrosurgery involves the application of high-frequency electric current to treat, cut or modify biological tissue during a surgical procedure. Electrosurgery is performed using an electrosurgical generator, an active electrode, and a return electrode. The electrosurgical generator (also referred to as a power supply or waveform generator) generates an alternating current (AC), which is applied to tissue through the active electrode and is returned to the electrosurgical generator through the return electrode. The alternating current usually has a frequency above 100 kilohertz to avoid muscle and/or nerve stimulation.

During electrosurgery, the alternating current generated by the electrosurgical generator is conducted through tissue disposed between the active and return electrodes. The tissue's impedance converts the electrical energy (also referred to as electrosurgical energy) associated with the alternating current into heat, which causes the tissue temperature to rise. The electrosurgical generator controls the heating of the tissue by controlling the electric power (i.e., electrical energy per time) provided to the tissue. Although many other variables affect the total heating of the tissue, increased current density correlates to increased heating. Electrosurgical energy is typically used for cutting, dissecting, ablating, coagulating, and/or sealing tissue.

The two basic types of electrosurgery are monopolar and bipolar electrosurgery. Both types of electrosurgery use an "active" and a "return" electrode. In bipolar electrosurgery, the surgical instrument includes an active electrode and a return electrode on the same instrument or in very close proximity, usually causing current to flow through a smaller amount of tissue. In monopolar electrosurgery, the return electrode is located elsewhere on the patient's body and is typically not part of the electrosurgical instrument itself. In monopolar electrosurgery, the return electrode is part of a device usually referred to as a return pad.

Electrosurgical generators may perform various self-tests. Electrosurgical generators test internal and external components to determine if one or more abnormalities are present. Some of the self-tests that electrosurgical generators perform occur during startup and are typically referred to as power-on self-tests. Self-tests may also occur during operation of the electrosurgical generator, including during a surgical procedure. These tests facilitate safe, efficient and/or accurate operation of the electrosurgical generator.

SUMMARY

The present disclosure relates to an electrosurgical generator that includes a primary source, a test source, an output circuit, and an abnormality detection circuit. The primary source supplies a primary signal and the test sources supplies a test signal. The output circuit is electrically coupled to the primary and test sources to receive the primary and test signals, respectively, therefrom. The abnormality detection circuit is electrically coupled to the output circuit and detects an abnormality in the output circuit as a function of the test signal. The abnormality detection circuit determines the location of the abnormality within the output circuit. The abnormality may be a short within the output circuit, an open circuit within the output circuit, an abnormality of a resistor within the output circuit, an abnormality of a sensor coupled within the output circuit, an abnormality of a coil within the output circuit, a circuit component of the output circuit being different than a predetermined value, the circuit component of the output circuit being different than a calibrated value, and/or the circuit component of the output circuit being outside of a predetermined range of values.

The load may be tissue and/or an electrosurgical RF output stage of the electrosurgical generator. The primary source and the test source may be integrated together or separate from each other. The primary signal may be amplitude modulated to generate the test signal, e.g., such as when the primary and test sources are integrated together. The test signal may be applied during a power-on self test of the electrosurgical generator. In some embodiments, the abnormality detection circuit may be calibrated to the output circuit.

The output circuit may include a feedback sensor configured to provide a feedback signal to the primary source. The primary source may operatively adjust the primary signal as a function of the feedback signal and the abnormality detection circuit may be electrically coupled to the feedback sensor to sense the test signal therethrough. The abnormality detection circuit may detect the abnormality as a function of the test signal received from the feedback sensor or multiple other sensors in the output circuit.

In another embodiment of the present disclosure, the test signal is generated digitally by the controller and digitally summed with the control output signal to modulate the primary signal.

In another embodiment of the present disclosure, the test source generates an impulse signal defining the test signal. The abnormality detection circuit receives the impulse response signal to determine an impulse response of test signal in the output circuit. The abnormality detection circuit detects the abnormality and determines the location of the abnormality as a function of the impulse response of the test signal in the output circuit via a plurality of sensors in the output circuit.

In yet another embodiment of the present disclosure, the test source modulates the test signal. The test signal may be modulated using a multisine algorithm, a pseudo-random noise algorithm, a chirp algorithm, and/or a swept sine impetus algorithm. The test source may generate the test signal such that the test signal is substantially or statistically orthogonal to the primary signal, e.g., the test signal may be a pseudo-random noise signal defining the test signal such that the test signal is statistically uncorrelated to the primary signal, thereby improving the signal-to-noise ratio (SNR) of the selected test method.

In yet another embodiment of the present disclosure, the test signal is one of multisine or multitone modulation that has a plurality of frequencies not including the primary signal frequency or its harmonics. The abnormality detection circuit may then detect the frequency response function of the intervening generator components at each of the fundamental test frequencies for linearity and the odd and even test frequency components for non-linearity.

The abnormality detection circuit may further comprise a tunable band-pass filter adapted to tune to the test signal for sinusoidal-based test tones, e.g., swept sine or chirp. The test source can operatively communicate a frequency-information signal indicating a frequency of the test signal and the primary signal frequency to the tunable band-pass filter. The tunable band-pass filter may tune to a frequency of the test signal indicated by the frequency-information signal. Additionally or alternatively, the abnormality detection signal may include a notch filter having a center frequency substantially equal to the frequency of the primary signal.

In yet another embodiment of the present disclosure, the test source may modulate the test signal using a maximum length sequence algorithm. The abnormality detection circuit is cross-correlated with the modulation of the test source to recover the impulse response of the intervening generator components.

In yet another embodiment of the present disclosure, the output circuit includes first and second circuit branches. The first circuit branch includes first and second switches. The first switch is electrically coupled between the output circuit and a first end of the load thereby conducting the primary signal between the output circuit and the first end of the load when closed. The second switch is electrically coupled to a second end of the load and a ground thereby conducting the primary signal between the second end of the load and the ground when the first and second switches are closed.

The second circuit branch includes third and fourth switches. The third switch is electrically coupled between the output circuit and the second end of the load thereby conducting the primary signal between the output circuit and the second end of the load when closed. The fourth switch is electrically coupled to the first end of the load and ground thereby conducting the primary signal between the first end of the load and the ground when the third and fourth switches are closed. The abnormality circuit may further include a switch tester operatively coupled to the first, second, third, and fourth switches. The switch tester may be adapted to detect an abnormality in one of first, second, third, and fourth switches as a function of the test signal and a drive signal applied to one of the first, second, third, and fourth switches through primary-side voltage and current sensors and/or the output feedback voltage and current sensors.

In yet another embodiment of the present disclosure, the electrosurgical generator includes an output feedback voltage sensor, an output feedback current sensor, a converter voltage sensor, and a converter current sensor. The output feedback voltage sensor is electrically coupled to the output circuit and is configured to generate a first signal corresponding to a voltage of the output circuit. The output feedback current sensor is electrically coupled to the output circuit and is configured to generate a second signal corresponding to a current of the output circuit. The converter voltage sensor is electrically coupled to an output terminal of a converter and configured to generate a third signal corresponding to an output voltage of a converter used in generator configurations based on the modified Kahn-technique of amplitude modulation. The converter current sensor is electrically coupled to an output terminal of the converter and configured to generate a fourth signal corresponding to an output current of the converter. The abnormality detection circuit can determine the location of the abnormality as a function of the first, second, third, and fourth signals. Additionally or alternatively, the generator may include more voltage and current sensors. The sensors may be electrically coupled between the DC source and the converter, and between the inverter and the resonant filter. The sensors may be used for alternative feedback/feedforward control or for abnormality detection fault isolation.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1A:
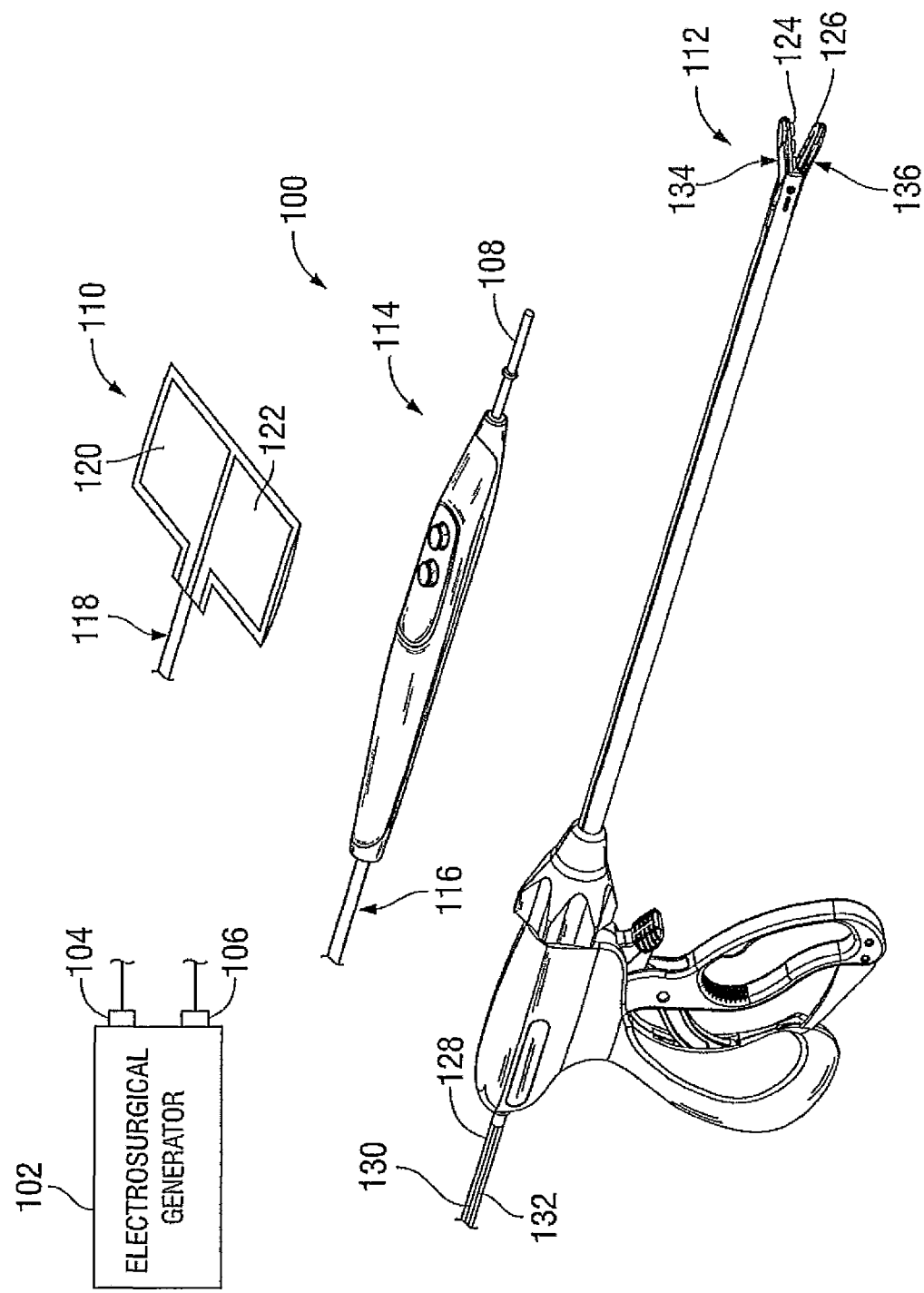
FIG. 1A shows a graphical illustration of an electrosurgical system in accordance with embodiments of the present disclosure.

FIG. 1A shows a graphic illustration of a bipolar and monopolar electro surgical system 100 in accordance with an embodiment of the present disclosure. The electrosurgical system 100 includes an electrosurgical generator 102 capable of detecting an abnormality and the location of the abnormality therewithin (described below). The generator 102 performs monopolar and bipolar electrosurgical procedures, including vessel sealing procedures. The generator 102 may include a plurality of outputs (e.g., terminals 104 and 106) for interfacing with various electrosurgical instruments (e.g., a monopolar active electrode 108, a return pad 110, bipolar electrosurgical forceps 112, a footswitch (not shown), etc. Further, the generator 102 includes electronic circuitry that generates radio frequency power specifically suited for various electrosurgical modes (e.g., cutting, blending, division, etc.) and procedures (e.g., monopolar treatment, bipolar treatment, vessel sealing, etc.).

The system 100 includes a monopolar electrosurgical instrument 114 having one or more electrodes 108 for treating tissue of a patient (e.g., electrosurgical cutting probe, ablation electrode(s), etc.). Electrosurgical RF current is supplied to the instrument 114 by the generator 102 via a supply line 116, which is connected to an active terminal 104 of the generator 102, allowing the instrument 114 to coagulate, ablate and/or otherwise treat tissue. The RF current is returned from electrode 108 through tissue to the generator 102 via a return line 118 of the return pad 110 at a return terminal 106 of the generator 102. The active terminal 104 and the return terminal 106 may include connectors (not explicitly shown) configured to interface with plugs (also not explicitly shown) of the instrument 114 and the return electrode 110, which are disposed at the ends of the supply line 116 and the return line 118, respectively.

The system 100 also includes return electrodes 120 and 122 within return pad 110 that are arranged to minimize the chances of tissue damage by maximizing the overall contact area with the patient's tissue. In addition, the generator 102 and the return electrode 110 may be configured for monitoring so-called "tissue-to-patient" contact to insure that sufficient contact exists therebetween to further minimize chances of tissue damage.

The system 100 also includes a bipolar electrosurgical forceps 112 having one or more electrodes (e.g., electrodes 124 and 126) for treating tissue of a patient. The instrument 112 includes opposing jaw members 134 and 136 having an active electrode 124 and a return electrode 126 disposed therein, respectively. The active electrode 124 and the return electrode 126 are connectable to the generator 102 through cable 128, which includes a supply line 130 and a return line 132 coupled to the active terminal 104 and the return terminal 106, respectively. The instrument 112 is coupled to the generator 102 at a connector having connections to the active terminal 104 and return terminal 106 (e.g., pins) via a plug (not explicitly shown) disposed at the end of the cable 128, wherein the plug includes contacts from the supply line 130 and the return line 132.

The generator 102 may be any suitable type (e.g., electrosurgical, microwave, etc.) and may include a plurality of connectors to accommodate various types of electrosurgical instruments (e.g., instrument 114, electrosurgical forceps 112, etc.). Further, the generator 102 may be configured to operate in a variety of modes such as ablation, monopolar and bipolar cutting, coagulation, and other modes. It is envisioned that the generator 102 may include a switching mechanism (e.g., relays) to switch the supply of RF energy between the connectors, such that, for instance, when the instrument 114 is connected to the generator 102, only the monopolar plug receives RF energy. The active terminal 104 and return terminals 106 may be coupled to a plurality of connectors (e.g., inputs and outputs) of the generator 102 to power a variety of instruments.

The generator 102 includes suitable input controls (e.g., buttons, activators, switches, touch screen, and the like) for controlling the generator 102. In addition, the generator 102 may include one or more display screens for providing the user with a variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instruments 112 and 114 may also include a plurality of input controls that may be redundant with certain input controls of the generator 102. Placing the input controls at the instruments 112 and 114 allow for easier and faster modification of RF energy parameters during the surgical procedure without requiring interaction with the generator 102.

Figure 1B:
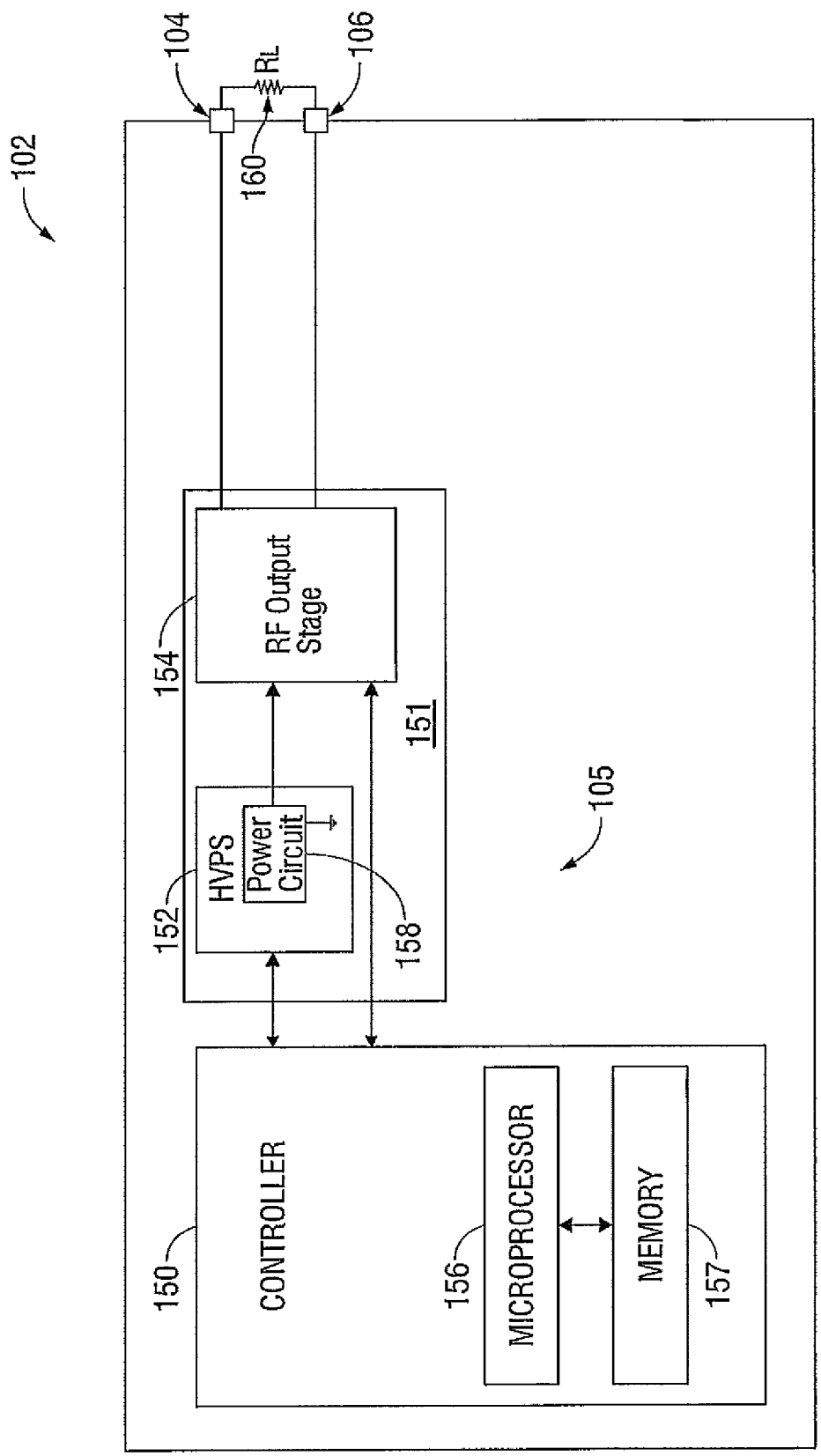
FIG. 1B shows a block diagram of an electrosurgical generator of the electrosurgical system of FIG. 1 in accordance with embodiments of the present disclosure.

FIG. 1B shows a block diagram of the electrosurgical generator 102 of FIG. 1A including a generator circuit 105 in accordance with an embodiment of the present disclosure. The generator circuit 105 includes a controller 150 and an output stage 151 which is controlled by the controller 150. The output stage 151 includes a high voltage power supply (HVPS) 152 and a radio frequency (RF) output stage 154. The controller 150 includes a microprocessor 156 and a memory 157. The microprocessor may be any suitable microcontroller, microprocessor (e.g., Harvard or Von Neuman architectures), PLD, PLA, CPLD, FPGA, or other suitable digital logic. Memory 157 may be volatile, non-volatile, solid state, magnetic, or other suitable storage memory.

Controller 150 may also include various circuitry (e.g., amplifiers, buffers and the like) to provide an interface between microprocessor 156 and other circuitry of the generator circuit 105. Controller 150 receives various feedback signals that are analyzed by microprocessor 156 to provide control signals in response thereto. The controls signals from controller 150 control the HVPS 152 and the RF output stage 154 to provide electrosurgical energy to tissue, which is represented by a load resistor $R_L$ 160.

The HVPS 152 includes a power circuit 158. The power circuit 158 supplies a suitable electric current to the RF output stage 154. The RF output stage 154 converts the current from the power circuit 158 to electrosurgical energy for application to the load resistor $R_L$ 160. For example, the HVPS 152 provides a DC signal to the RF output stage 154 that generates the electrosurgical energy using push-pull or H-bridge transistors coupled to a primary side of a step-up transformer with a resonant load matching network (not explicitly shown).

Figure 2A:
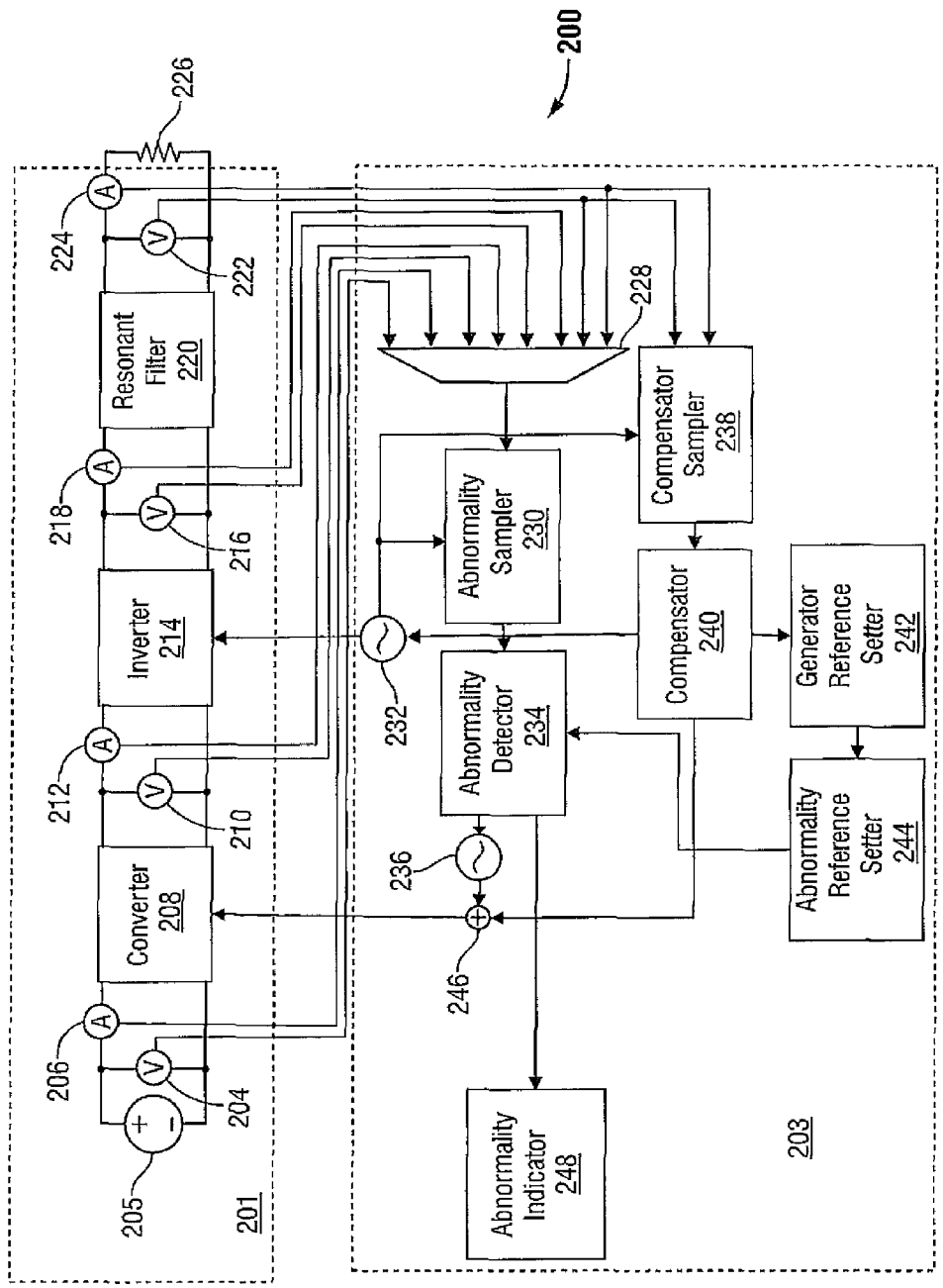
FIG. 2A shows a block diagram of a generator circuit including an output circuit and an abnormality detection circuit based on a modified Kahn-technique, high efficiency, amplitude modulated electrosurgical generator in accordance with an embodiment of the present disclosure.

FIG. 2A illustrates generator circuitry 200 of an electrosurgical generator (e.g., a high-efficiency, amplitude-modulated, resonant RF electrosurgical generator) according to some embodiments of the present disclosure. The generator circuitry 200 includes an output circuit 201 coupled to a controller circuit 203, which includes an abnormality detector 234 for detecting abnormalities in the output circuit 201. The abnormalities may be detected using a modified Kahn technique as described in more detail below. The output circuit 201 includes voltage source 205, converter 208, inverter 214, and resonant filter 220. The output of the voltage source 205 is electrically connected to the input of the converter 208, the output of the converter 208 is electrically connected to the input of the inverter 214, the output of the inverter 214 is electrically connected to the input of the resonant filter 220, and the output of the resonant filter 220 is configured to deliver energy to tissue, the impedance of which is represented by the load resistor 226. The output circuit 201 also includes a plurality of voltage sensors 204, 210, 216, and 222, and a plurality of current sensors 206, 212, 218, and 224, each of which are electrically connected to the output of one of the voltage source 205, the converter 208, the inverter 214, and the resonant filter 220.

The voltage source 205 provides direct current to the converter 208, which increases the voltage of the direct current. The converter 208 provides the converted direct current to the inverter 214, which inverts converted direct current to an alternating current. The inverter 214 receives synchronization signals from an oscillator 232 of the controller circuit 203. In this way, the inverter 214 can generate an alternating current having an appropriate frequency for electrosurgery. The resonant filter 220 enables the transfer of substantially maximum power to load resistor 226 by resonating characteristics of the output circuit 201 to characteristics of the load resistor 226. Additionally, the sensed results from the voltage sensor 222 and the current sensor 224 have higher importance than the other sensed results because the output of the resonant filter 220 is directly connected to the patient. For this reason, the sensed results of the voltage sensor 222 and the current sensor 224 are also provided to the compensator sampler 238.

The number and placement of voltage and current sensors may vary depending upon the circuitry used in the output circuits 201 and 251 to generate electrosurgical energy. Also, voltage and current sensors may be placed within the different subcircuits of the output circuits 201 and 251 to obtain different and more granular measurements. For example, one or more voltage and current sensors may be placed at appropriate points within the inverter 252 or resonant filter 220.

The controller circuit 203 includes the multiplexer 228, abnormality sampler 230, abnormality detector 234, compensator sampler 238, compensator 240, generator reference setter 242, abnormality reference setter 244, abnormality indicator 248, two oscillators 232 and 236, and an adder 246. The multiplexer 228 receives sensed results from all the voltage and current sensors, selects one or more sensed results, and sends the selected results to abnormality sampler 230. The compensator sampler 238 receives the sensed results of the output of the resonant filter 220. Both the abnormality sampler 230 and the compensator sampler 238 are synchronized with the frequency of the alternating current generated by the inverter 214 to filter the received sensed results from the voltage and current sensors by the carrier oscillator 232. The carrier oscillator 232 may be a voltage-controlled oscillator or a numerically-controlled oscillator.

The compensator 240 receives the filtered samples from the compensator sampler 238 and compensates fluctuations of the filtered samples over a time period. One example of compensating circuits is a proportional-integral-derivative ("PID") controller. The result of the compensator 240 is then provided to the carrier oscillator 232 and the generator reference setter 242.

The carrier oscillator 232 takes the output of the compensator 240 into consideration and provides appropriate synchronization signals to the inverter 214, the abnormality sampler 230, and the compensator sampler 238.

The generator reference setter 242 receives the compensated results from the compensator 240 and sets an appropriate reference power profile that can be used as a reference in detecting abnormalities in the output circuit 201. The reference power profile is then provided to the abnormality reference setter 244. With the reference power profile, the abnormality reference setter 244 sets tolerance ranges for voltage and current of each of circuits in the output circuit 201. The abnormality reference is then provided to the abnormality detector 234 and the abnormality detector 234 checks whether sampled results of the multiplexer 228 are within a tolerance range specified in the abnormality reference. If the result is in the tolerance range, the abnormality detector 234 outputs no abnormality and, if the results are not within the tolerance range, outputs abnormality.

For example, if the multiplexer 228 selects results from the output of the inverter 214, the abnormality reference setter 244 sets tolerance ranges of the output of the inverter 214 based on the reference power profile provided by the generator reference setter 242. The selected results by the multiplexer 228 are sampled by the abnormality sampler 230. The abnormality detector 234 then compares the sampled output of the abnormality sampler 230 with the tolerance ranges of the abnormality reference setter 244. If the sampled output is out of the tolerance range, the abnormality detector 234 then finds abnormality in the inverter 214.

The test oscillator 236 receives the result of the abnormality detector 234 and generates a test signal having a frequency is different from the frequency generated by the carrier oscillator 232. The test oscillator 236 may generate a signal of which frequency is specific to a circuit where an abnormality is found. For this embodiment, the test oscillator 236 may generate four different signals with four different frequencies which are different from the frequency generated by the carrier oscillator 232. In order to have meaningful results from each sensor and from the abnormality sampler 230 and the compensator sampler 238, the four different frequencies are less than the frequency generated by the carrier oscillator 232.

The signal generated by the test oscillator 236 and the result of the compensator are added by the adder 246 and the added signal is then provided to the converter 208 so that the test signal for detecting abnormality is propagated into the output circuit 201.

The abnormality detector 234 may also provide the abnormality result to the abnormality indicator 248 to indicate which circuit has abnormality to an operator of the electrosurgical generator and the operator can take appropriate actions to correct the abnormality and to prevent possible harm to a patient.

Figure 2B:
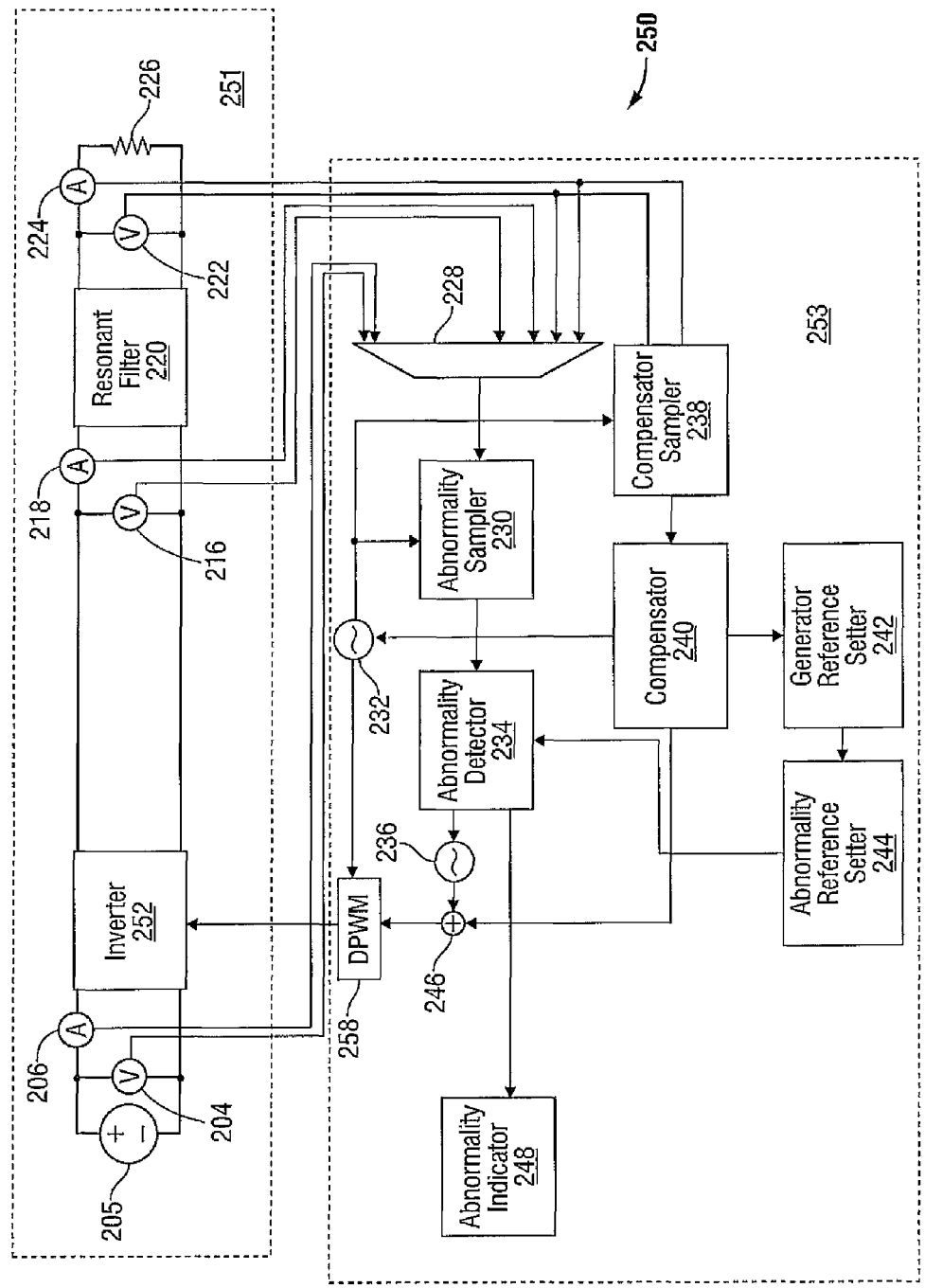
FIG. 2B shows a block diagram of a generator circuit and an abnormality detection circuit based on a Class S, high-efficiency, pulse-width modulated electrosurgical generator in accordance with a further embodiment of the present disclosure.

FIG. 2B illustrates generator circuitry 250 for a Class S, high-efficiency, pulse width modulated resonant electrosurgical generator according to other embodiments of the present disclosure. The generator circuitry 250 includes an output circuit 251 and a control circuit 253. Instead of converter 208 and inverter 214 of FIG. 2A, the output circuit 251 of FIG. 2B includes inverter 252. Also, the control circuit 253 includes a digital pulse width modulation (DPWM) unit 258 for generating and providing a DPWM control signal to the inverter 252.

A method of detecting an abnormality in a system includes applying a test signal to the system, measuring the frequency response functions between any two sets of sensors in the system, and comparing the measured frequency response functions (FRFs) with the expected variation limits of the FRFs for a normal system between any two sets of sensors in the system. The abnormality of the system under test may be defined as occurring when at least one of several possible conditions is detected:

1. The FRF magnitude, which is typically defined as |H(s)| for gain and |Z(s)| for impedance (which are described in more detail below), at the test frequency deviates by more than a predetermined maximum value.
2. The FRF phase, which is typically defined as arg(H(s)) for gain and arg(H(s)) for impedance (which are described in more detail below), at the test frequency deviates by more than a predetermined maximum value.
3. There is more distortion and noise energy (defined below) present in the output spectrum after going through the network between sensors, e.g., sensors 204, 206, 216, and 218, than a predetermined maximum value.

By testing the FRF against any combination of these conditions, the abnormality detection system can detect not only components or groups of components that have open- and short-circuited in the signal path between the sets of sensors, but also components or groups of components that have partially failed or that output the wrong value. The abnormality detection system may also detect intermittent abnormalities as long as they are manifest over a sufficient portion of the measurement period. The last condition (condition 3.) may be helpful in revealing non-linear behavior resulting from an abnormality that is manifest as distortion outside of the fundamental frequency of interest.

In addition to abnormality detection, one may perform (simultaneously) calibration of one, or more, circuits within a system between sets of sensors using either or both internal or externally attached loads. One may connect a known load resistance, or impedance, and measure the FRF, then, by the ratio of the FRF to the expected nominal FRF, apply frequency-dependent magnitude and phase corrections.

The FRFs may be transfer functions (i.e., gains) or impedances. The following transfer functions may be useful for abnormality detection and isolation:

1. Voltage gain defined as $$H_V(s) = \frac{V_B(s)}{V_A(s)},$$

where $V_B(s)$ is the Laplacian domain voltage at output sensor B and $V_A(s)$ is the Laplacian domain voltage at input sensor A.

2. Current gain defined as $$H_I(s) = \frac{I_B(s)}{I_A(s)},$$

where $I_B(s)$ is the Laplacian domain current at output sensor B and $I_A(s)$ is the Laplacian domain current at input sensor A.

3. Input impedance defined as $$Z_i(s) = \frac{V_A(s)}{I_A(s)}.$$

4. Load impedance defined as $$Z_1(s) = \frac{V_B(s)}{I_B(s)}.$$

5. Output impedance defined as $$Z_o(s) = Z_1(s)\frac{V_B(s) - V_A(s)}{V_A(s)}.$$

The location of an abnormality can be narrowed down to the groups of components that are disposed between the sets of sensors of these FRFs using the gain transfer functions and further isolated using impedance and distortion infor-mation. More sets of sensors may be added to further isolate even smaller groups of components as required by risk assessment and desired product features. The testing may be performed as part of a self-test, e.g., off-line, at any time and it may also be performed continuously during operation of the system, e.g., on-line, as long as the test signal is either designed to be of a nominal energy level as compared to the energy contained in the primary signal, i.e., the therapeutic signal. Alternatively, the test signal may be designed to be included as part of the primary signal energy, or may even be the control signal itself. Testing against a subset of these criteria may yield a useful set of possible abnormalities, which depends upon the position of the sets of sensors used for the test within the system and the use cases and requirements of the operational environment in question.

A first step for determining an abnormality is to ensure a priori, i.e., at the time of design of the system, that the signal to noise ratio (SNR) of the measurement is sufficient for determining an abnormality, i.e., the measured response to the test signal is significantly lower in variance for a normal system under test than the just-detectable variance of the abnormalities.

The swept single-sine method (including a chirp) has been used to obtain high-fidelity FRFs and distortion analysis. However, the length of time required to obtain good SNR for low frequency signals and the intrusiveness of the method in performing on-line measurement of an active system have opened the door to development and use of other alternative methods over the past couple of decades. The swept single-sine method is best applied off-line during calibration procedures or during power-on self-tests (POSTs).

A single-impulse method does not generally yield a very good SNR for FRF measurements and may be less helpful in distortion analysis. Often, multiple impulse tests are performed and averaged over time to improve the SNR, which tends to lengthen test times and make the single-impulse method less desirable over swept single-sine methods. Therefore, it may be best to apply the swept single-sine method off-line during calibration procedures or POST, especially for purposes of distortion analysis. Also, an averaging of simple random-noise tests may be performed over long periods of time to obtain satisfactory SNR to make an FRF measurement.

The Maximum Length Sequence (MLS) test, where the noise is a priori chosen as a pseudo-random sequence to allow for correlation of the received test signal with the sourced signal, is generally considered a better test in terms of obtaining satisfactory results over relatively short test times with minimal invasiveness and little or no additional averaging time necessary. The MLS test may be applied online during RF activations or off-line during calibration procedures or POST.

With respect to SNR, the measured energy, £, for the single-sine test signal can be written, using Parseval's Theorem for the discrete Fourier transform (DFT) relation, as the sum of three components: DC, AC, and noise. This may be expressed algebraically as:

$$\varepsilon = \sum_{n=0}^{N-1} |x_n|^2 = \frac{1}{N}|\hat{X}_0|^2 + \frac{1}{N}|\hat{X}_1|^2 + \frac{1}{N}\sum_{k \neq 1} |\hat{X}_k|^2 \quad (1)$$

where $x_n$ is the discrete-time series of DFT window length N for the measured periodic signal including exactly one complete cycle of the AC component (i.e., coherently sampled), $\hat{X}_0$ is the DC component, $\hat{X}_1$ is the complex AC component of the test signal (i.e., the excited or fundamental component), and $\hat{X}_k$ are the complex distortion and noise components in the unexcited harmonics of the AC fundamental component. It is also possible to uniquely identify harmonics, or select harmonics, of this distortion as well. These components may be extracted from the measured discrete-time series as follows:

$$\hat{X}_0 = \sum_{n=0}^{N-1} x_n \qquad (2)$$

and $$\hat{X}_1 = \sum_{n=0}^{N-1} x_n \left[ \cos\left(\frac{2\pi}{N} \cdot n\right) - i \cdot \sin\left(\frac{2\pi}{N} \cdot n\right) \right]. \qquad (3)$$

This is a complex single-frequency DFT.

The noise energy may be derived from (1)-(3) by subtracting the AC and DC components from the total signal power:

$$\hat{\varepsilon}_{noise} = \sum_{n=0}^{N-1} |x_n|^2 - \left[ \frac{1}{N}|\hat{X}_0|^2 + \frac{1}{N}|\hat{X}_1|^2 \right], \qquad (4)$$

while the resulting SNR is the ratio of the AC signal power to the noise energy of expression (4):

$$SNR = \frac{\frac{1}{N}|\hat{X}_1|^2}{\hat{\varepsilon}_{noise}}. \qquad (5)$$

This SNR must be greater than the abnormality threshold to be measured, which is some fraction $c_1$ of the expected normal AC test component:

$$SNR > \left[ \frac{c_1}{N}|\hat{X}_1|^2 \right]^{-1}. \qquad (6)$$

For the multisine FRF measurement one may extend expression (1) to multiple excitation frequencies, which may be randomized in respective phases:

$$\varepsilon = \sum_{n=0}^{N-1} |x_n|^2 = \frac{1}{N}|\hat{X}_0|^2 + \frac{1}{N}\sum_m |\hat{X}_m|^2 + \frac{1}{N}\sum_{k \neq m} |\hat{X}_k|^2, \qquad (7)$$

where $\hat{X}_m$ are a series of m multisine AC components of the test signal, and $\hat{X}_k$ are the distortion and noise components in the unexcited harmonics (i.e. excluding the fundamental components m) of the multisine AC components. These individual components, also assuming coherent sampling, may similarly be extracted from the measured discrete-time series according to the following equation:

$$\hat{X}_m \sum_{n=0}^{N-1} x_n \left[ \cos\left(\frac{2\pi}{N} m \cdot n\right) - i \cdot \sin\left(\frac{2\pi}{N} m \cdot n\right) \right]. \qquad (8)$$

This is also a complex single-frequency DFT at frequency $$f_m = \frac{2\pi}{N} m.$$

The noise energy may be selected values s∈k of unexcited DFT bins given by:

$$\hat{\varepsilon}'_{noise} = \frac{1}{N} \sum_{s \in k \neq m} |\hat{X}_s|^2. \qquad (9)$$

These selected bins are determined a priori. One approach is to simply use all of the unexcited bins. Another approach is to drop one or more bins due to a need for reduced computation time or non-idealities in the measurement technique resulting from short lengths of N and frequency smearing, or bleeding, between DFT frequency bins from intermodulation components. An advantage of looking at selected bins or combinations of bins in the multisine technique is that distortion products due to failed or failing components will create stronger than normal harmonic content relative to the AC fundamental component that may be observed in these bins. For example, saturation due to voltage overdrive will result in a measurable relative increase in the odd harmonics.

The resulting SNR for multisine at any particular excitation frequency e∈m may be expressed as:

$$SNR' = \frac{\frac{1}{N}\sum_{e \in m} |\hat{X}_e|^2}{\hat{\varepsilon}'_{noise}}. \qquad (10)$$

This SNR must be greater than the abnormality threshold to be measured, which is some fraction $c_e$ of the expected normal component:

$$SNR > \left[ \frac{1}{N}\sum_{e \in m} c_e |\hat{X}_e|^2 \right]^{-1}. \qquad (11)$$

Conversely, the selected unexcited components could be used to detect abnormalities, when they are greater than the expected value. While this is true of both single-sine tests as well as multisine, multisine allows for a more rapid determination of this situation with a sufficiently long DFT (or, more practically, Fast Fourier Transform (FFT)).

The SNR may be improved by averaging multiple measurements over time, assuming that the noise is random. This is because the averaging process results in a coherent addition of the sinusoids of interest and a non-coherent addition of the noise. Such an improvement is referred to as processing gain. But processing gain may also be achieved by any individual or combination of methods employing pre-emphasis and de-emphasis of the originating stimulus test signal spectrum, e.g., increasing the amplitudes of the higher frequency components of the test signal to compensate for a low-pass frequency response of the system or circuit under test by applying an inverse function of the normal response. This is referred to as leveling or equalization. Averaging is essential for random-noise tests, especially when combined with leveling, and it can significantly improve MLS tests to the point of being nearly indistinguishable in fidelity to swept single sine tests.

There are a number of ways to do averaging. One way is vector averaging of the received abnormality detector DFT spectra. Each averaged pair increases the SNR by 3 dB. The advantage of vector averaging is that it maintains phase information. In vector averaging, the complex values, e.g., the real and imaginary components of equation (3), are averaged as opposed to averaging of the overall magnitudes or root mean square (r.m.s) averaging. Vector averaging requires coherent, and optionally synchronous, sampling, i.e., the abnormality detector data sampler window must be triggered and data samples taken at a rate that is related by integer multiples of the AC test components and their phases. Since the controller circuits 203 and 253 generate the test signal and the control signal while digitally sampling the sensors, synchronous and coherent sampling can be guaranteed.

Careful consideration may be given a priori to the Crest Factor of the test signal employed. The Crest Factor is given by the peak, $g_\infty(u)$, to root mean square (r.m.s), $g_2(u)$, ratio for a discrete-time series, $u(n)$. The Crest Factor in this case is computed according to the equation:

$$CF(u) = \frac{g_\infty(u)}{g_2(u)} = \frac{\max_{n \in [0, N-1]} |u(n)|}{\sqrt{\frac{1}{N} \sum_{n=0}^{N-1} |u(n)|}} \tag{12}$$

Test signals in the form of an impulse signal, a multisine signal, and a random noise signal (e.g., a maximum length sequence (MLS) signal) all have high Crest Factors relative to the single-sine test signal. High Crest Factors reduce the signal-to-noise ratio (SNR) and overall quality of the measurement. The objective of these test signals, such as in the case of more versatile multisine tests, is to minimize the Crest Factor to optimize the SNR.

Generally, swept single-sine test signals have the best SNR with the lowest Crest Factor with respect to all other types of test signals. Leveling and averaging can be applied to the other types of test signals to reduce the Crest Factor and to optimize the SNR. Tests using the impulse test signal, however, must be repeated periodically and the inverse of the leveling function must be applied to the test signal. Applying leveling and averaging to random noise and MLS test signals may improve SNR comparable to the SNR of the swept single-sine test signals, but the Crest Factors may be an order of magnitude higher than the Crest Factor of a swept single-sine test signal that is leveled and averaged.

In other embodiments, the test signal may be a multisine excitation test signal, which straddles the solution sets of MLS signals and swept single-sine signals. The multisine excitation test sequence includes a sum of sinusoids, which are not necessarily harmonically related, each with its own phase with respect to the start of the sequence. The multisine excitation test sequence may be given by the equation:

$$u(n) = \sum_{m=1}^{M} a_m \cos(2\pi \cdot f_m \cdot n + \varphi_m), \tag{13}$$

where M is the number of sinusoids, $\varphi_m$ is the phase of each sinusoid with respect to the start of the sequence, $a_m$ are the excitation fundamental amplitudes, and $f_m$ are the excitation frequencies. The phase $\varphi_m$ may be randomized between $[-\pi, \pi)$ to reduce the Crest Factor and thereby improve the SNR.

Figure 3:
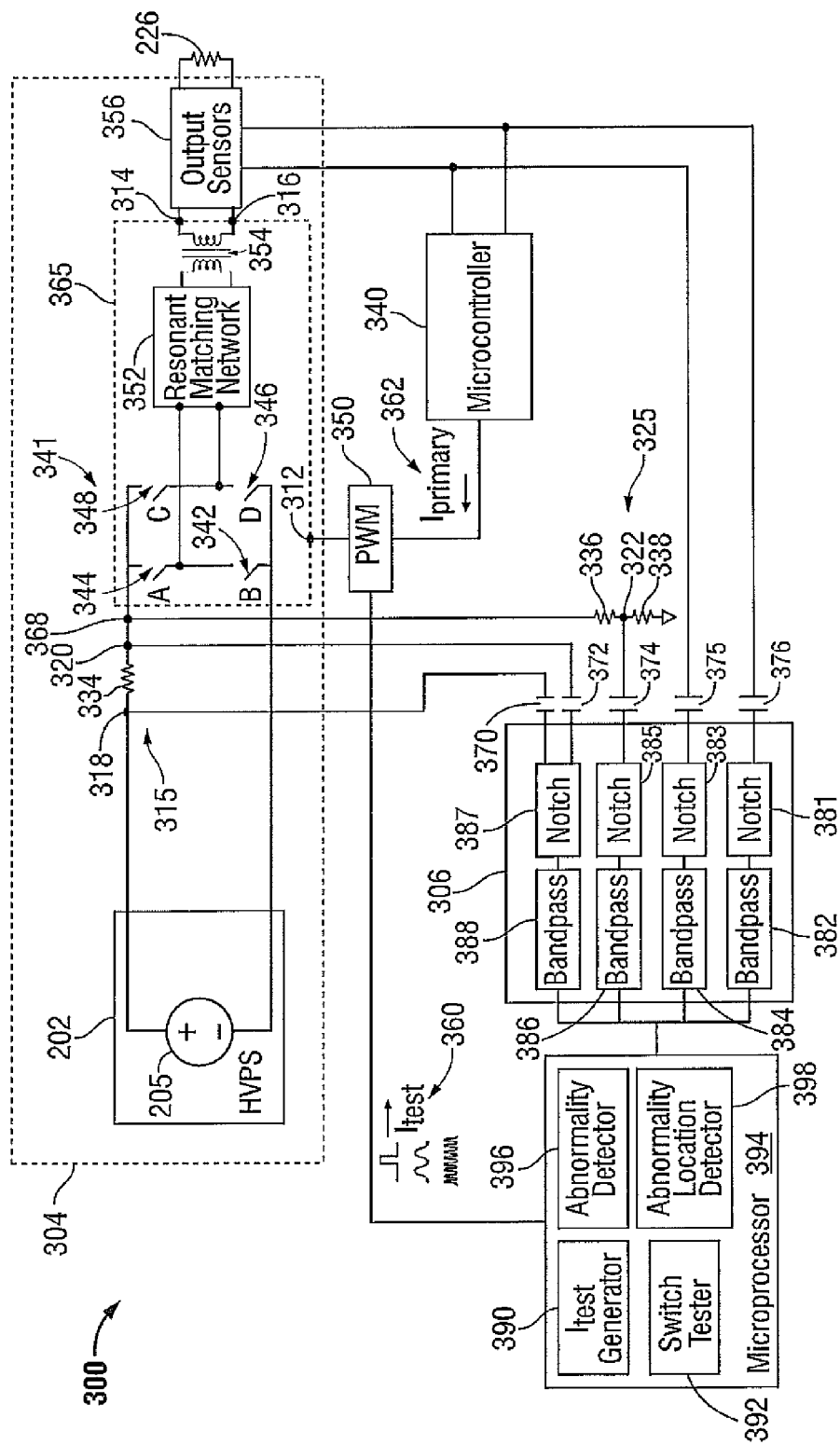
FIG. 3 shows a block diagram of a generator circuit including an output circuit and an abnormality detection circuit in accordance with a still further embodiment of the present disclosure.

FIG. 3 shows a block diagram of a generator circuit 300 in accordance with a still further embodiment of the present disclosure. The generator circuit 300 includes an output circuit 304, an abnormality sampler 306, a microprocessor 394, which includes an abnormality detector 396, a microcontroller 340, and a pulse width modulator (PWM) 350. The microcontroller 340 includes a primary signal generator that generates a primary signal $I_{primary}$ 362, which is provided to an input of the PWM 350. The microprocessor 394, which may be implemented by the microcontroller 340, includes a test signal generator 390, a switch tester 392, an abnormality detector 396, and an abnormality location detector 398. The test signal generator 390 generates a test signal $I_{test}$ 360 that is provided to another input of the PWM 350.

The PWM 350 modulates the primary signal 362 with the test signal 360 and generates PWM signals based on the modulated primary signal 362 to operate the switches 342, 344, 346, and 348 of the H-bridge inverter 341. The output circuit 304 is electrically coupled to the load resistor 226. The microprocessor 394 and the abnormality sampler 306 are electrically coupled to the outputs of the HVPS 202 and the output sensors 356 of the output circuit 304.

The microcontroller 340 provides a primary signal 362 for application to the input node 312 of the circuit being tested 365, which includes an H-bridge inverter 341, a resonant matching network 352, and an output transformer 354, via the PWM 350. In embodiments of the present disclosure, the circuit being tested 365 is any circuit which supplies electrical energy to a load and may include (or may be) a supply line, one or more conductors, a cable, a multiple path circuit and/or any suitable circuitry to supply electrical energy from an input node (e.g., input node 312) to an output node (e.g., output nodes 314 and 316).

The microprocessor 394 supplies the test signal $I_{test}$ 360 to the PWM 350, which modulates the primary signal 362 with the test signal 360, generates a PWM signal based on the modulated primary signal 362, and provides the PWM signal to the circuit being tested 365 via input node 312. The abnormality detector 396 can detect one or more abnormalities within the circuit being tested 365 or the output circuit 304 via the abnormality sampler 306. The abnormality sampler 306 receives and samples the sensed input and output currents and voltages from output circuit 304. The microprocessor 394 includes the abnormality detector 396 which processes these sensed current and voltage signals to detect an abnormality within the output circuit 304.

The output circuit 304 includes a current sensor 315 and a voltage sensor 325 coupled to the input of the circuit being tested 365. The current sensor 315 includes a resistor 334 that is coupled in series between the HVPS 202 and the circuit being tested 365. The voltage sensor 325 includes resistors 336 and 338 coupled together in series in a voltage divider configuration. The abnormality sampler 306 samples the voltages at nodes 318 and 320 to measure the current through the resistor 334. Additionally, the microcontroller 340 receives the output current and voltage sensed by the output sensors 356 at the output nodes 314 and 316. The microcontroller 340 utilizes the sensed output current and voltage to control the generation of the primary signal 362.

Referring to FIGS. 4A-6B, several alternative current and voltage sensors are shown that are usable by the output circuits 201, 251, and 304 of FIGS. 2A, 2B, and 3.

Figure 4B:
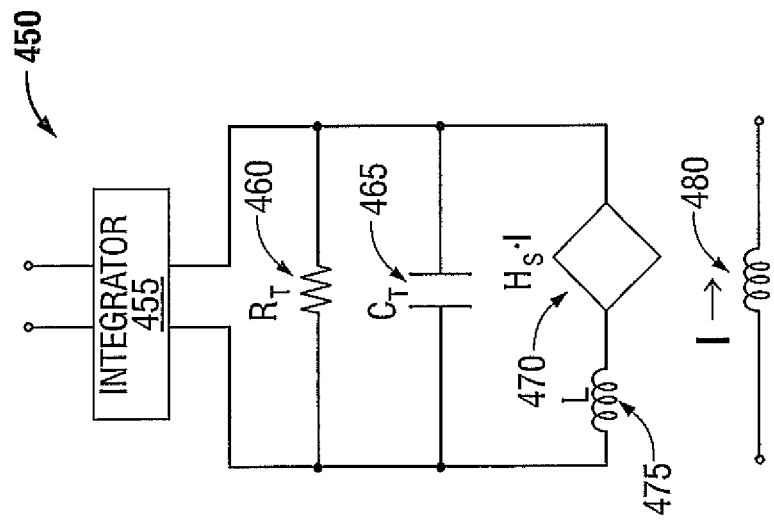
FIGS. 4A-6B show current and voltage sensors used for abnormality detection in an electrosurgical generator in accordance with embodiments of the present disclosure.
Figure 4A:
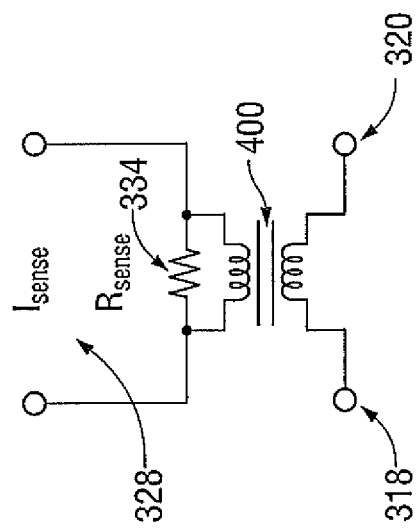

FIG. 4A shows a circuit diagram of an embodiment of a current sensor for sensing current flowing, for example, between nodes 318 and 320 of the output circuit 304. The current sensor includes an iron current transformer 400 having a first coil coupled between the nodes 318 and 320 and having a second coil coupled in parallel with resistor 334 ($R_{sense}$). The current $I_{sense}$ 328, which represents the current flowing between the nodes 318 and 320, is obtained by measuring the voltage across the resistor 334.

FIG. 4B shows a circuit diagram of another embodiment of a current sensor 450 that includes an air core Rogowski coil to sense current. The current sensor 450 includes an integrator 455 and a Rogowski coil, which is represented by a resistance $R_T$ 460, a capacitance $C_T$ 465, and an inductance L 475. Hs indicates the sensitivity of the Rogowski coil and Hs·I is a voltage 470 induced by current I flowing through an inductor 480 coupled to an output circuit. A terminal voltage across the capacitance $C_T$ 465 causes current to flow through the resistance $R_T$ 460 and the integrator 455 sums the current flowing through the resistance $R_T$ 460 and provides a voltage. The current flow through the Rogowski coil is then determined by measuring the voltage across the outputs of the integrator 455.

Figure 5B:
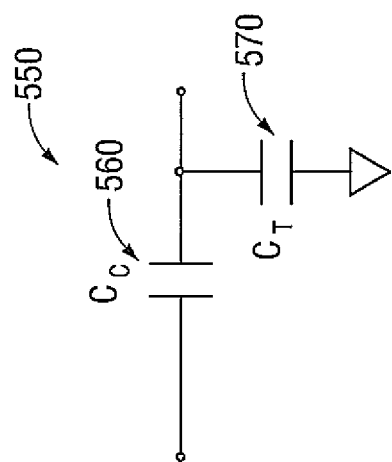
Figure 5A:
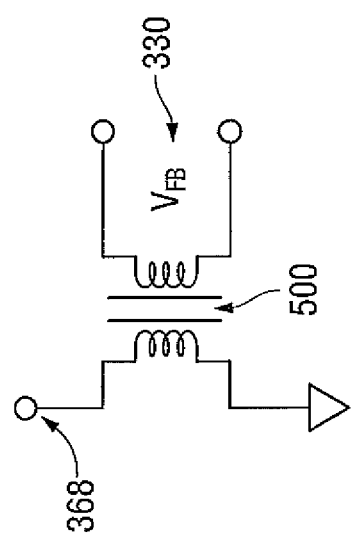

FIG. 5A shows a voltage sensor that includes a single-ended voltage transformer 500 having an iron core for coupling to the circuit being tested 365 (FIG. 3) via, for example, a ground and node 368 to generate the sensed voltage signal V 330. FIG. 5B shows another embodiment of a voltage sensor including a capacitive, single-ended voltage transformer 550. The capacitive single-ended voltage transformer 550 includes two capacitors: an input-side capacitor 560 and a terminal-side capacitor 570. The input voltage is stepped down by the two capacitors 560 and 570 and a terminal voltage is output across the terminal-side capacitor 570.

Figure 6B:
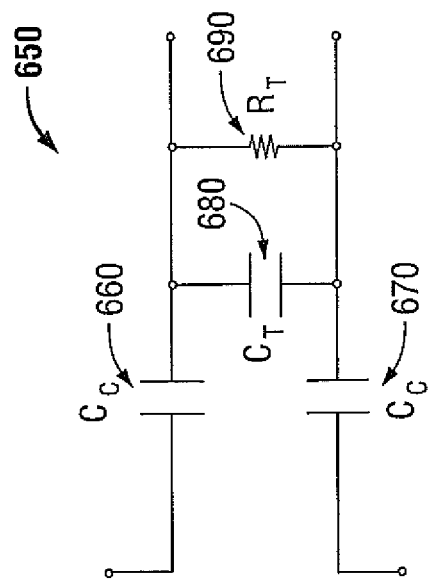
Figure 6A:
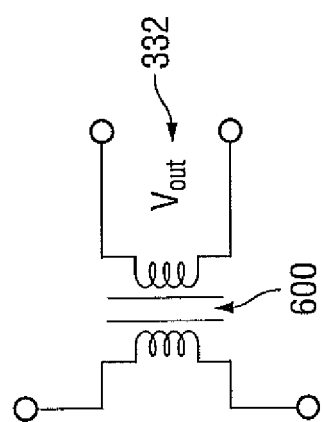

FIG. 6A shows a voltage sensor including an isolated, differential, iron core voltage transformer 600 for coupling, for example, to the output of the circuit being tested 365 (FIG. 3) via RF active node 314 and RF return node 316 to provide output signal V 332 representative of the difference between voltages of the RF active node 314 and the RF return node 316. FIG. 6B is another embodiment of a voltage sensor including a differential, capacitive voltage transformer 650 that includes two input-side capacitors 660 and 670, a terminal-side capacitor 680, and a terminal-side resistor 690. This voltage sensor measures a difference in voltage between the input terminals and steps it down to a desired output voltage value.

Referring again to FIG. 3, the abnormality detector 396 can detect an abnormality within the circuit being tested 365 utilizing the test signal 360. The abnormality detection may occur during a power-on self-test (i.e., during a POST routine), and the abnormality detector 396 may be calibrated to the circuit being tested 304. In some embodiments, capacitors 370 and 372 couple the abnormality sampler 306 to the current sensor 315, capacitor 374 couples the abnormality sampler 306 to the voltage sensor 325, and capacitors 375 and 376 couples the abnormality sampler 306 to the output sensors 356, which includes an output current sensor and an output voltage sensor (not shown). The capacitors 375 and 376 may filter out the primary signal 362 and/or may be DC blocking capacitors.

The abnormality sampler 306 includes notch filters 381, 383, 385, and 387, and bandpass filters 382, 384, 386, and 388. Each of the notch filters 381, 383, 385, and 387 are coupled to a respective bandpass filters 382, 384, 386, and 388. The microprocessor 394 receives an output voltage signal from the output sensors 356 via notch filter 381 and bandpass filter 382. The microprocessor 394 receives an output current signal from the output sensors 356 via notch filter 383 and bandpass filter 384. The microprocessor 394 receives an input voltage signal from node 322 of the voltage sensor 325, which is a voltage divider including resistors 336 and 338 via notch filter 385 and bandpass filter 386. The microprocessor 394 receives an input current signal from the current sensor 315 via notch filter 387 and bandpass filter 388. Additionally, microprocessor 394 may detect the voltage at node 318 via the notch filter 387 and the bandpass filter 388.

The microprocessor 394 may be a digital signal processor (not explicitly shown), and/or may be implemented in software, hardware, firmware, virtualization, PLAs, PLD, CPLD, FPGA and the like. Additionally or alternatively, the microcontroller 340 and the microprocessor 394 may be integrated together, e.g., such as within a digital signal processor, and may include a watchdog timer. The microprocessor 394 utilizes the test signal generator 390 thereby facilitating the operation of the abnormality detector 396 and the abnormality location detector 398 in detecting and determining the location of an abnormality within the output circuit 304. Additionally, the test signal generator 390 operatively instructs the PWM 350 to selectively control switches 342, 344, 346, and 348 to determine an abnormality within the switches 342, 344, 346, and 348.

The test signal 360 is applied to input node 312 thereby affecting the input current and voltage signals sensed at node 368 and the output voltage and current signals sensed at output nodes 314 and 316 by the output sensors 356. The test signal generator 390 controls the generation of the test signal $I_{test}$ 360 thereby affecting the input and output current and voltage signals to detect an abnormality within the output circuit 304, and to determine the location of the abnormality therewithin. The microprocessor 394 and the microcontroller 340 utilize a single set of non-redundant sensors. However, in other embodiments, the sensors may be redundant. The abnormality may be a short within the output circuit 304, an open circuit within the output circuit 304, an abnormality of a resistor (e.g., one or more of resistors 334, 336, 338) within the output circuit 304, an abnormality of a sensor coupled within the circuit being tested 304, an abnormality of a coil (e.g., of an output transformer (not shown) coupled between output nodes 314 and 316 to provide a step-up voltage) within the output circuit 304, a circuit component (e.g., the resistors 334, 336, and/or 338) of the output circuit 304 being different than a predetermined value, the circuit component (e.g., the resistors 334, 336, and/or 338) of the output circuit 304 being different than a calibrated value, the circuit component (e.g., the resistors 334, 336, and/or 338) of the output circuit being outside of a predetermined range of values, and/or the like.

The bandpass filters 382, 384, 386, and 388 are tunable to obtain frequency information. The frequency information includes the frequency of the test signal 360. The frequency information may be received via a digital or analog signal. The bandpass filters 382, 384, 386, and 388 are tuned to the test signal 360. The notch filters 381, 383, 385, and 387 have a center frequency that filters out the primary signal 362. As mentioned previously, the tunable bandpass filters 382, 384, 386, and 388, and the notch filters 381, 383, 385, and 387 may be implemented in software or by utilizing a digital signal processor.

Microprocessor 394 may detect an abnormality and its location by determining the system ID of the circuit being tested 365, using ohm's law calculation, and/or circuit analysis to detect discrepancies or failures of the resistors or sensors (e.g., resistors 336, 338, and 334). For example, the microprocessor 394 can control the PWM 350 to generate an impulse signal defining the test signal 360. The microprocessor 394 receives the impulse signal from the output sensors 356 to detect an abnormality and determine the location of the abnormality as a function of the impulse response of the output circuit. Microprocessor 394 may also detect an abnormality and its location by utilizing other algorithms including swept-sine, chirp, and/or pseudo-random noise impetus signals. Additionally or alternatively, microprocessor 394 may detect an abnormality and its location by utilizing various algorithms to determine the system ID of the circuit being tested 304, including algorithms utilizing swept-sine, chirp, and/or pseudo-random noise impetus signals.

Microprocessor 394 is in operative communication with microcontroller 340 (in some embodiments, the microcontroller 340 and the microprocessor 394 are integrated together). In one embodiment of the present disclosure, microprocessor 394 detects abnormalities while the microcontroller 340 is disabled; and the microprocessor 394 determines the accuracy of one of resistors 334, 336, and 338 or switches 342, 344, 346, and 348, and communicates to the microcontroller 340 adjustment values for adjusting the primary signal 362. Additionally, microprocessor 394 may test output circuit 304 with or without the load resistor 226.

Abnormality detector 396 may instruct PWM 350 to output A, B, C, and D signals to control the switches 342, 344, 346, and 348. More particularly, the test signal generator 390 can operatively disable microcontroller 340 (or at least disable output of the primary signal 362 from the microcontroller 340) and instruct PWM 350 to apply a test signal to selectively switch switches 342, 344, 346, and 348. The microprocessor 394 can utilize the sensed input and output voltages and currents to determine whether one or more of switches 342, 344, 346, and 348 has an abnormality. In some embodiments, other switches (not shown) may disconnect the load resistor 226. In other embodiments, groups of switches 342, 344, 346, and 348 are activated by microprocessor 394 so that microprocessor 394 can determine if one or more of the switches 342, 344, 346, and 348 are operating properly. In yet other embodiments, switches 342, 344, 346, and 348 are tested during a power-on self test.

As mentioned above, the test signal $I_{test}$ 360 may be narrowband limited or orthogonal to the primary signal $I_{primary}$ 362. For example, the test signal $I_{test}$ 360 may utilize a pseudo-random noise sequence that is orthogonal (uncorrelated) to the primary signal $I_{primary}$ 362. Additionally or alternatively, abnormality sampler 306 may be phase locked with the microprocessor 394, e.g., using a phase-locked loop to track a frequency-hopping microprocessor 394.

The test signal $I_{test}$ 360 may incorporate a minimum or maximum length sequence (MLS) and may be used to extract the impulse response of the circuit being tested 365. See CMDA: Principles of Spread Spectrum Communication, Addison-Wesley, 1995. The following equation can be used to generate an MLS of period, $P=2^r-1$:

$$a_n = \sum_{i=1}^{r} c_i a_{n-i}, \qquad (14)$$

where $a_n$ is the next desired sequence value and $c_i$ are the coefficients of the primitive polynomial of degree $r>1$. The values for $c_i$ may be from tables for primitive polynomials of various degrees in sources such as Error Correcting Codes, by E. J. Weldon and W. W. Peterson, MIT Press, Cambridge, Mass., 1972.

To find the impulse response of an unknown system, h[n], such as the output circuit 304, the test signal generator 390 may apply the MLS algorithm to the test signal $I_{test}$ 360. By using a[n], the output response is given by the convolution of h[n] and a[n]:

$$y[n]=h[n]*a[n]. \qquad (15)$$

By utilizing circular cross-correlation, the following equation is obtained:

$$\bar{\phi}_{sy}=h[n]*\bar{\phi}_{ss}. \qquad (16)$$

But, because, by definition, the autocorrelation $\bar{\phi}_{ss}$ is an ideal impulse function, i.e.:

$$\bar{\phi}_{ss} \approx \delta_r[n], \qquad (17)$$

it follows that:

$$h[n]=\bar{\phi}_{sy}. \qquad (18)$$

The method for determining the system impulse results includes: (1) drive the test signal $I_{test}$ 360 using a repeating sequence $a_{1-[n]}[n]$; (2) measure the response y[n]; and (3) perform a circular cross-correlation of y[n] with $a_r[n]$ to produce $\hat{h}[n-\Delta]$, which is the $\Delta$-delayed estimate of h[n].

In some embodiments, a least mean squares (LMS) filter may be employed to generate a model of a circuit of the electrosurgical generator that is being tested in order to determine whether there is an abnormality in the circuit. The circuit may be described as an unknown system h(n) to be modeled or identified and the LMS filter adapts the filter $\hat{h}(n)$, which represents an estimate of the model of the circuit, to make it as close as possible to h(n). An abnormality may be detected in a particular circuit by comparing the adapted filter $\hat{h}(n)$, which represents the current model of the particular circuit, to a predetermined filter $\hat{h}(n)'$, which represents the same type of circuit that is operating normally. If there is a difference between the adapted filter $\hat{h}(n)$ and the predetermined filter $\hat{h}(n)'$, characteristics of that difference may be used to determined the type of abnormality.

Figure 7A:
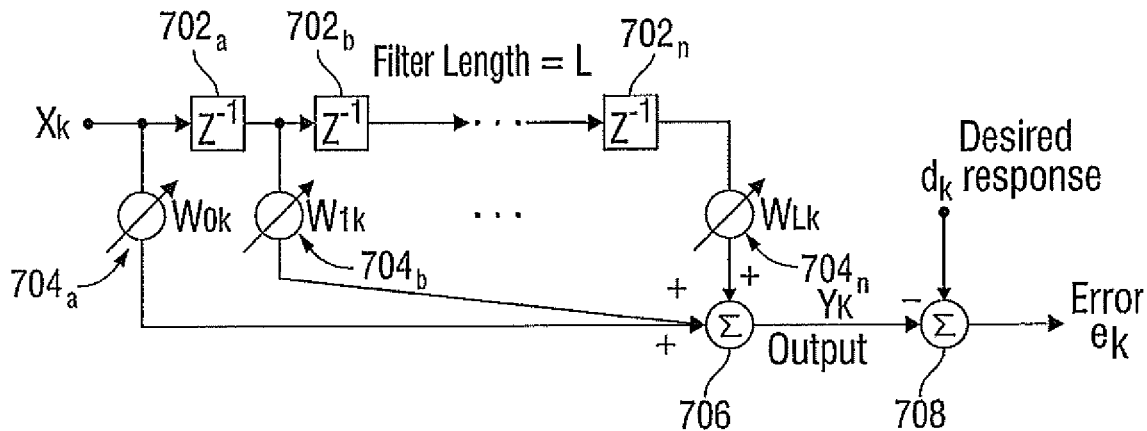
FIGS. 7A-7F show system-level block diagrams representing a maximum length sequence algorithm for modulating and receiving the test signal utilized by the abnormality detection circuit of FIG. 3 in accordance with an embodiment of the present disclosure.

FIG. 7A is a detailed block diagram of an LMS filter according to an embodiment of the present disclosure. The LMS filter, which may be a finite impulse response (FIR) filter, includes a series of time delay units 702a-702n and a series of weighting units 704a-704n coupled to a digital input test signal $x_k$. During operation, the first weighting unit 704a multiplies the digital input signal $x_k$ by the first weight value $w_{0k}$ of the weight vector $\bar{w}_{k+1}$. The time delay units 702b-702n shift the digital input test signal $x_k$ and corresponding weighting units 704b-704n multiply the delayed digital input test signal $x_k$ by corresponding weight values $w_{1k}, \ldots w_{Lk}$ of the weight vector $\bar{w}_{k+1}$. The results of time delaying and weighting the digital input test signal $x_k$ are added together by an adder 706 to obtain the output signal $y_k$.

The output signal $y_k$ is fed back to a LMS weight adaptation unit, in which the output signal $y_k$ is subtracted from the desired response signal $d_k$, which would be the output from the actual circuit being modeled, by a subtractor 708 to obtain an error signal $e_k$. The error signal $e_k$ and the input test signal are then used in the following LMS update equation to compute the weight vector updates:

$$\bar{w}_{k+1}=\bar{w}_k+2\mu e_k \bar{x}_k, \qquad (19)$$

where μ is chosen by the designer and is bounded:

$$0 < \mu < \frac{1}{\lambda_{max}},$$

where $\lambda_{max} \le \text{trace}(\overline{\Lambda}) = \text{trace}(\overline{R})$. Or, more simply:

$$0 < \mu < \frac{1}{(L+1)(\text{Signal Power of } \overline{x}_k)}, \quad (20)$$

where L is the filter length.

Figure 7B:
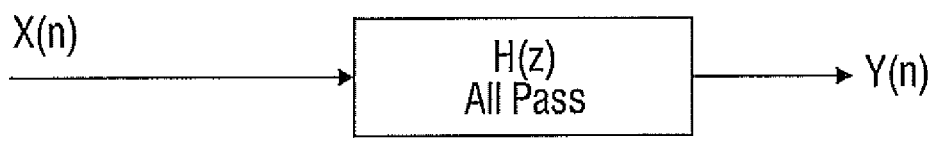
Figure 7C:
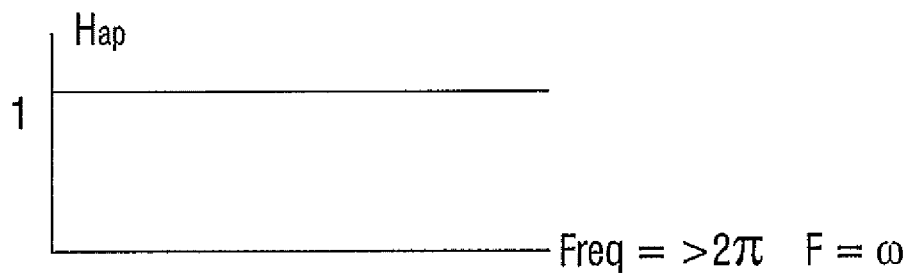
Figure 7D:
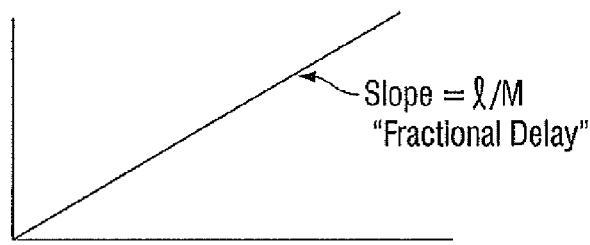
Figure 7E:
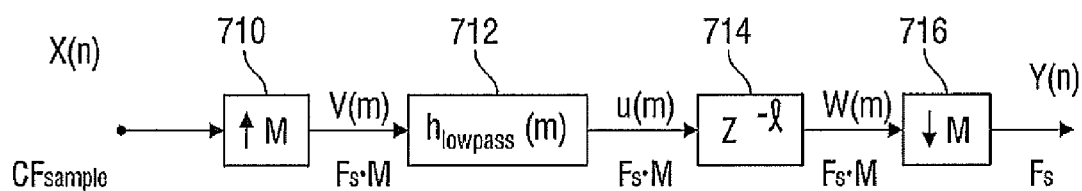

FIGS. 7B-7F show the structure for implementing the time delay units 702b-702n with a fractional fixed delay of l/m samples. FIGS. 7B-7E show the multi-rate structure for realizing a fixed delay of l/m samples. As shown in FIG. 7B, the multi-rate structure is an all-pass filter having unity gain (FIG. 7C) and a fractional delay (which is given by the slope shown in the graph of FIG. 7D). FIG. 7E shows the details of the multi-rate structure. As shown, an input test signal x(n) is applied to an interpolator 710, which up-samples the input test signal x(n) by a factor of M to obtain an up-sampled or interpolated signal v(m). The up-sampled signal v(m) is then filtered by a digital lowpass filter 712 to remove the images (i.e., the extra copies of the basic spectrum) created by the interpolator 710. The resulting filtered signal u(m) is then delayed by l samples by a delay unit 714 and down-sampled by a factor of M in the decimator 716 to obtain an equalized output signal y(n).

Figure 7F:
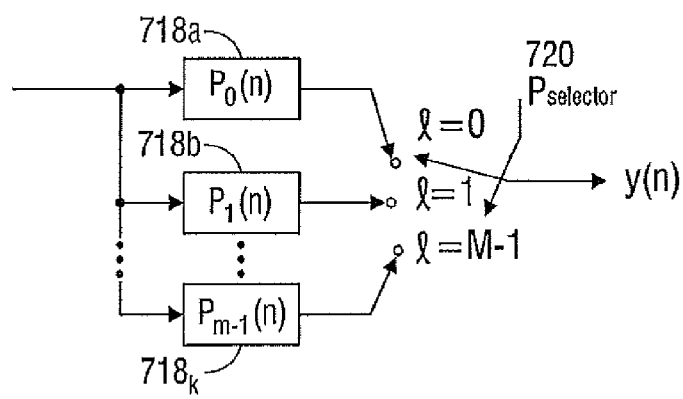

FIG. 7F is a diagram of an efficient polyphase implementation of the multi-rate structure of FIG. 7A. This implementation includes a series of transversal FIR filters 718a-718k that filter the input test signal x(n). The transversal FIR filters 718a-718k are given by the following difference equation:

$$p_r(n) = h_{LP}(nM+r), \quad (21)$$

where $0 \le r \le (M-1)$. The delay of l is implemented as a new initial position of the commutator switch ("P selector") 720 corresponding to the sample at n=0.

Figure 8:
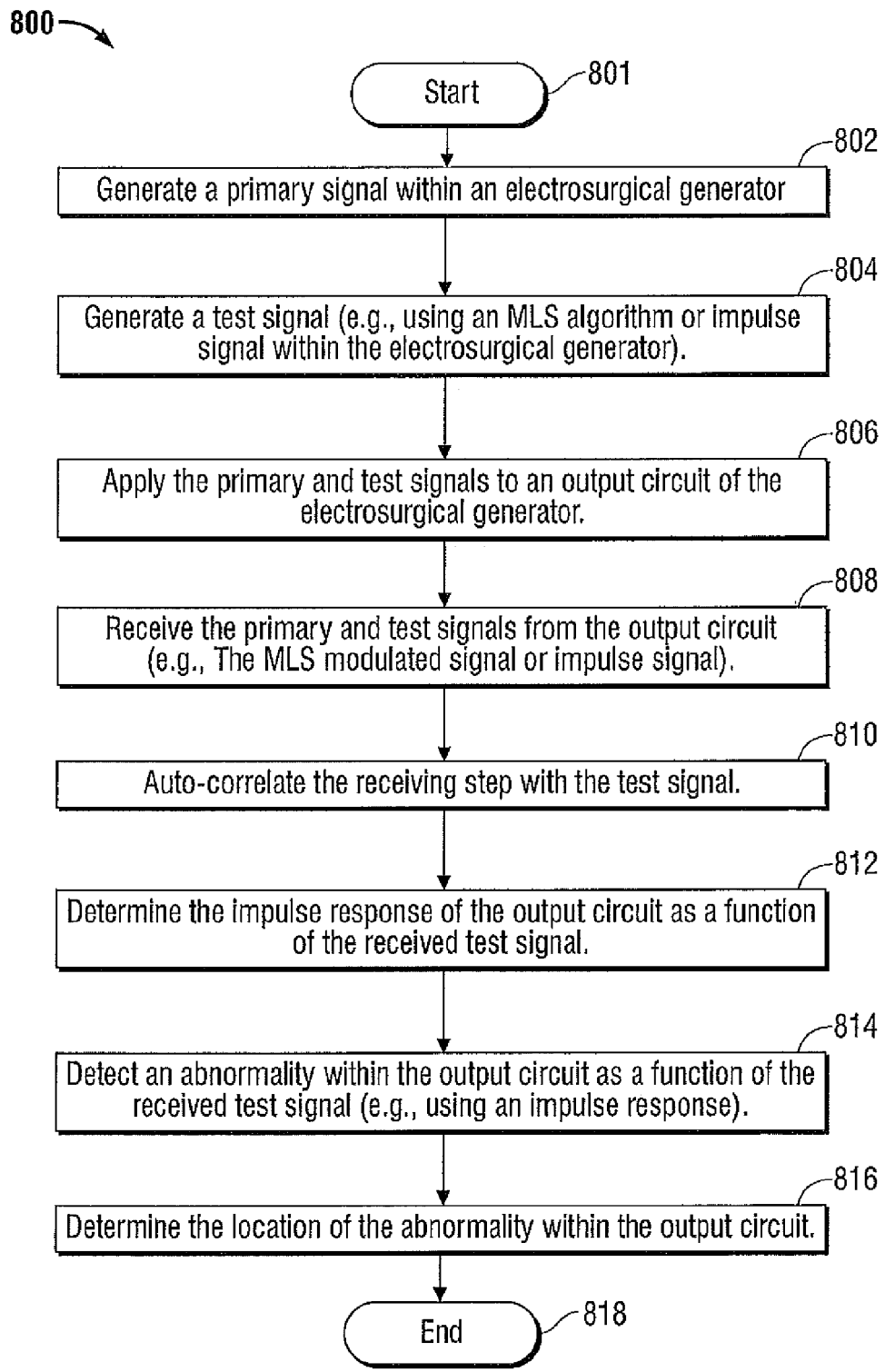
FIG. 8 shows a flow diagram of a method for abnormality detection in accordance with embodiments of the present disclosure.

FIG. 8 shows a flow chart diagram of a method 800 for abnormality detection in accordance with the present disclosure. The method 800 includes steps 801-818. After starting in step 801, a primary signal is generated within an electrosurgical generator in step 802. In step 804, a test signal is generated within the electrosurgical generator, e.g., using an MLS algorithm or impulse signal. Next, in step 806, the primary signal and the test signal are applied to an output circuit of the electrosurgical generator. In step 808, the primary signal and the test signal (e.g., the MLS modulated signal or impulse signal) are received from the output circuits. In step 810, the primary signal is autocorrelated with the test signal. In step 812, the impulse response of the output circuit is determined as a function of the received test signal. In step 814, an abnormality is detected with the output circuit as a function of the received test signal (e.g., using an impulse response). Then, before ending in step 818, the location of the abnormality within the output circuit is determined in step 816.

Figure 9:
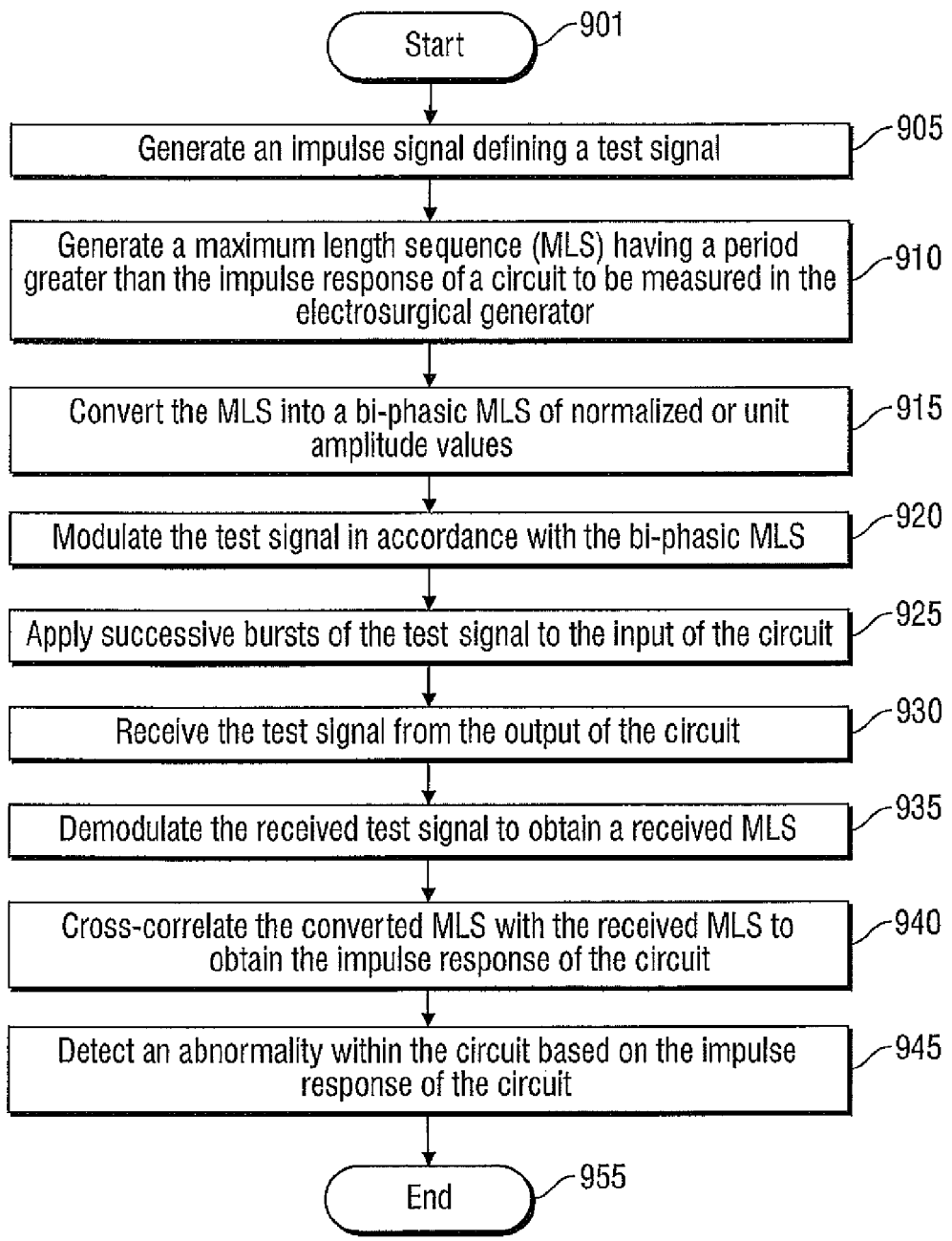
FIGS. 9 and 10 show flow diagrams of a method for abnormality detection using a maximum length sequence (MLS) technique in accordance with further embodiments of the present disclosure.

As described above, the test oscillator 236 may be modulated using a maximum length sequence (MLS) and may be used to extract the FRF of the circuit at any sensor distal to the test oscillator 236. A method for performing an MLS test is illustrated in FIG. 9.

After starting in step 901, an impulse signal defining a test signal is generated in step 905. In step 910, an MLS with a period greater than the impulse response of the desired circuit to be measured is generated (or obtained from a look-up table) based on the a priori known length of the circuit's impulse response in the time domain using, for example, the following equation:

$$n[k] = n(k) \oplus n(k+2), \quad (22)$$

where the operator $\oplus$ denotes an exclusive-or (XOR) (modulo-2 sum) operation, and k is the sequence index for the "M-sequence" n[k] of length $K = 2^N - 1$, consisting of N stages, initialized to 1s.

The M-sequence may then be used to create a K×K matrix consisting of rows, each of which is successively left circularly shifted (or delayed) of the original sequence in the first row. For example, a seven symbol M-sequence given by 1, 1, 1, 0, 0, 1, 0 may generate a matrix M given by:

$$M = \begin{bmatrix} 1 & 1 & 1 & 0 & 0 & 1 & 0 \\ 1 & 1 & 0 & 0 & 1 & 0 & 1 \\ 1 & 0 & 0 & 1 & 0 & 1 & 1 \\ 0 & 0 & 1 & 0 & 1 & 1 & 1 \\ 0 & 1 & 0 & 1 & 1 & 1 & 0 \\ 1 & 0 & 1 & 1 & 1 & 0 & 0 \\ 0 & 1 & 1 & 1 & 0 & 0 & 1 \end{bmatrix} = AB.$$

This matrix may then be decomposed into K×N and N×K matrices that may be referred to as "tag" matrices A and B, respectively, B is the first N rows of matrix M, i.e.:

$$B = \begin{bmatrix} 1 & 1 & 1 & 0 & 0 & 1 & 0 \\ 1 & 1 & 0 & 0 & 1 & 0 & 1 \\ 1 & 0 & 0 & 1 & 0 & 1 & 1 \end{bmatrix}.$$

A may be obtained by evaluating the following equation:

$$A = B^T \sigma^{-1}, \quad (23)$$

where $B^T$ is a transposed matrix of B and $\sigma^{-1}$ is the matrix inverse of σ, which is an N×N matrix of B, or the first N columns of B, i.e.:

$$\sigma = \begin{bmatrix} 1 & 1 & 1 \\ 1 & 1 & 0 \\ 1 & 0 & 0 \end{bmatrix}.$$

Taking the matrix inverse of σ results in the following matrix:

$$\sigma^{-1} = \begin{bmatrix} 0 & 0 & 1 \\ 0 & 1 & 1 \\ 1 & 1 & 0 \end{bmatrix}.$$

Thus, equation (23) may be evaluated using the matrices $B^T$ and $\sigma^{-1}$ to obtain matrix A:

$$A = \begin{bmatrix} 1 & 0 & 0 \\ 0 & 1 & 0 \\ 0 & 0 & 1 \\ 1 & 1 & 0 \\ 0 & 1 & 1 \\ 1 & 1 & 1 \\ 1 & 0 & 1 \end{bmatrix}.$$

In step 915, the generated MLS of 0s and 1s are converted to a bi-phasic sequence of normalized or unit amplitude values, e.g., 0 is converted to 1 and 1 is converted to −1. In step 920, the test signal is modulated in accordance with the bi-phasic MLS sequence. Then, in step 925, at least two successive bursts of the test signal modulated with the MLS are applied to the input of the desired circuit of the electrosurgical generator while receiving, in step 930, the test signal at the output from the desired circuit using a sensor or sensor pair coupled to the output. An initial burst may be used to allow transient settling, while the second or more successive bursts may be used for the measurements. The average of successive bursts may be calculated to improve the SNR.

In step 935, the received test signal is demodulated to obtain a received MLS. Then, in step 940, the received MLS is cross-correlated with the converted MLS to obtain the impulse response of the desired circuit. Before ending in step 955, an abnormality within the desired circuit is detected in step 945 based on the impulse response of the desired circuit.

Figure 10:
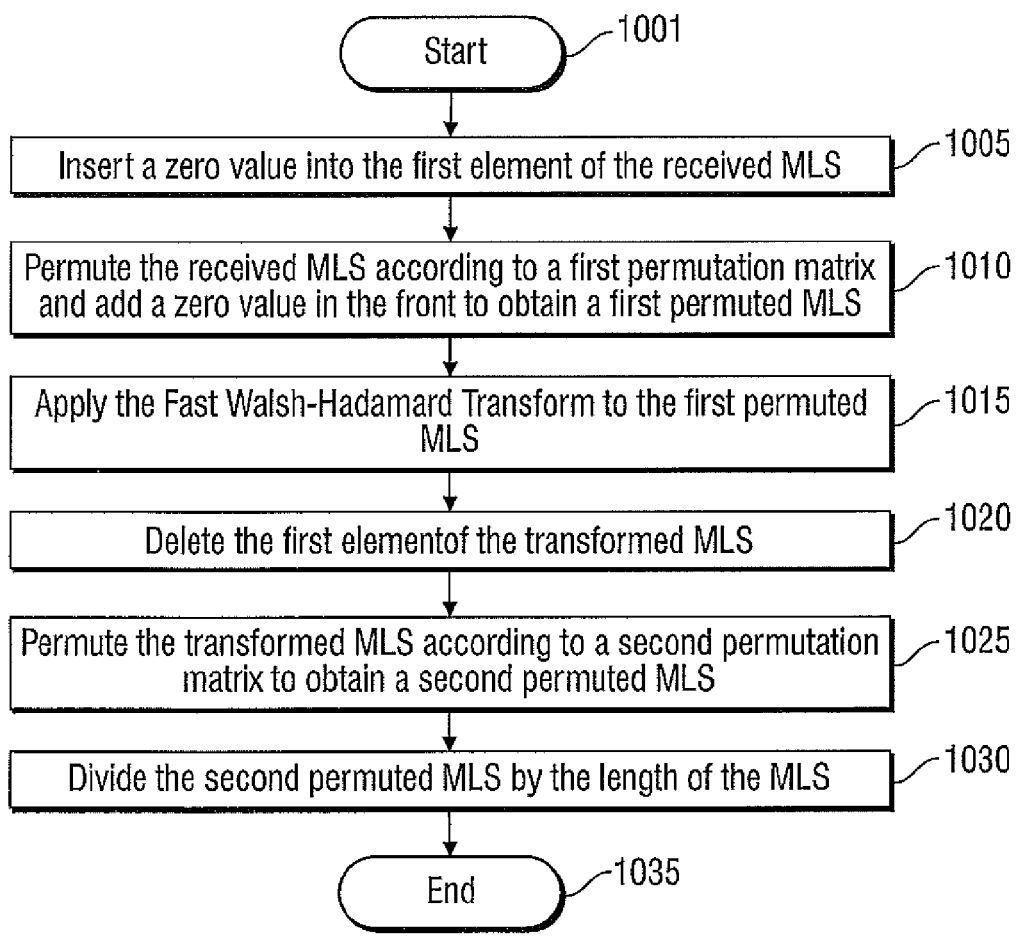

In embodiments, the received MLS may be cross-correlated with the converted MLS to obtain the impulse response of the desired circuit by using a suitable transformation algorithm. FIG. 10 illustrates such an algorithm. After starting in step 1001, an MLS (or an average MLS) is received and a zero value is inserted into the first element of the received MLS in step 1005. Then, in step 1010, the MLS is permuted (i.e., re-ordered) according to a first permutation matrix Ps to obtain a first permuted MLS. This is done to simplify the computation of the transform, such as the Fast Walsh-Hadamard Transform, and is analogous to the operations of "padding zeros" and permutation for simplifying FFTs.

In step 1015, the transform, such as the Fast Walsh-Hadamard Transform is applied to the first permuted MLS matrix. This is a cross-correlation function that selects the time-aligned impulse response data, while rejecting non-time-aligned or uncorrelated noise.

In step 1020, the first element of the transformed MLS is deleted and the result is permuted, or re-ordered, in step 1025, according to a second permutation matrix $P_L$ to obtain a second permuted MLS which is a row matrix as the tag matrix B. Before ending in step 1035, the second permuted MLS is divided by the length of the MLS, i.e., K+1, in step 1030 to obtain an estimated time-domain impulse response. This is analogous to the reordering done in FFTs. In embodiments, the estimated time-domain impulse response may be changed to the frequency domain by performing an FFT.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator comprising:
   a primary signal generator including a first oscillator configured to generate a primary signal having a first frequency;
   a test signal generator including a second oscillator configured to generate a test signal to detect a location of an abnormality in the electrosurgical generator, wherein the test signal has a second frequency different from the first frequency;
   a radio frequency (RF) output circuit electrically coupled to the primary signal generator and the test signal generator, the RF output circuit configured to receive the primary signal and the test signal, respectively, therefrom, wherein the RF output circuit is electrically coupled to a load to supply the primary signal and the test signal to the load; and
   an abnormality detection circuit electrically coupled to the RF output circuit to detect an abnormality within the RF output circuit based on an impulse response of the RF output circuit in response to the test signal, wherein the abnormality detection circuit is configured to determine a location of the abnormality within the RF output circuit based on the impulse response of the RF output circuit in response to the test signal.

2. The electrosurgical generator according to claim 1, wherein the electrosurgical generator further comprises a summer configured to sum the primary signal and the test signal for application to the RF output circuit.

3. The electrosurgical generator according to claim 1, wherein the abnormality detection circuit detects the abnormality and determines the location of the abnormality as a function of the impulse response of the RF output circuit.

4. The electrosurgical generator according to claim 1, wherein the RF output circuit further comprises a feedback sensor configured to provide a feedback signal to the primary signal generator,
   wherein the primary signal generator operatively adjusts the primary signal as a function of the feedback signal,
   wherein the abnormality detection circuit is electrically coupled to the feedback sensor to sense the test signal therethrough, and
   wherein the abnormality detection circuit detects the abnormality as a function of the test signal received from the feedback sensor.

5. The electrosurgical generator according to claim 1, wherein the test signal generator modulates the test signal according to at least one of a pseudo-random noise algorithm, a chirp algorithm, and a swept sine impetus algorithm.

6. The electrosurgical generator according to claim 1, wherein the test signal generator generates a pseudo-random noise signal defining the test signal such that the test signal is orthogonal to the primary signal.

7. The electrosurgical generator according to claim 1, wherein the abnormality detection circuit further comprises a tunable band-pass filter adapted to tune to the test signal.

8. The electrosurgical generator according to claim 7, wherein the test signal generator operatively communicates a frequency-information signal indicating a frequency of the test signal to the tunable band-pass filter, and
   wherein the tunable band-pass filter tunes to a frequency of the test signal indicated by the frequency-information signal.

9. The electrosurgical generator according to claim 1, wherein the abnormality detection circuit further comprises a notch filter having a center frequency about equal to a frequency of the primary signal.

10. The electrosurgical generator according to claim 1, wherein the primary signal generator and the test signal generator are integrated together, and
wherein the primary signal is amplitude modulated to generate the test signal.

11. The electrosurgical generator according to claim 1, the RF output circuit further comprising:
a first circuit branch including:
a first switch electrically coupled between the RF output circuit and a first end of the load thereby conducting the primary signal between the RF output circuit and the first end of the load when closed; and
a second switch electrically coupled to a second end of the load and ground thereby conducting the primary signal between the second end of the load and the ground when the first and second switches are closed; and
a second circuit branch including:
a third switch electrically coupled between the RF output circuit and the second end of the load thereby conducting the primary signal between the RF output circuit and the second end of the load when closed; and
a fourth switch electrically coupled to the first end of the load and the ground thereby conducting the primary signal between the first end of the load and the ground when the third and fourth switches are closed,
wherein the abnormality detection circuit further includes a switch tester operatively coupled to the first, second, third, and fourth switches, the switch tester being configured to detect an abnormality in one of first, second, third, and fourth switches as a function of the test signal and a drive signal applied to one of the first, second, third, and fourth switches.

12. The electrosurgical generator according to claim 1, wherein the test signal generator modulates the test signal using a Maximum length sequence algorithm, and wherein the abnormality detection circuit is auto-correlated with the modulation of the test signal generator.

13. The electrosurgical generator according to claim 12, wherein the abnormality detection circuit is phase locked with the test signal.

14. The electrosurgical generator according to claim 1, wherein the test signal is selected from the group consisting of narrowband limited and orthogonal.

15. The electrosurgical generator according to claim 1, further comprising:
a voltage sensor electrically coupled to the RF output circuit and configured to generate a first signal corresponding to a voltage of the RF output circuit;
a current sensor electrically coupled to the RF output circuit and configured to generate a second signal corresponding to a current of the RF output circuit; and
an output voltage sensor electrically coupled to an output terminal of the RF output circuit and configured to generate a third signal corresponding to an output voltage of the output terminal,
wherein the abnormality detection circuit determines the location of the abnormality as a function of the first, second, and third signals.

16. The electrosurgical generator according to claim 1, wherein the test signal is applied during a power-on self test of the electrosurgical generator.

17. The electrosurgical generator according to claim 1, further comprising a capacitor electrically coupled between the RF output circuit and the abnormality detection circuit, wherein the capacitor is configured to sufficiently filter the primary signal and sufficiently conduct the test signal therethrough.

18. The electrosurgical generator according to claim 1, wherein the test signal is a pseudo-random signal and the abnormality detection circuit is correlated to the test signal.

19. The electrosurgical generator according to claim 1, wherein the test signal is modulated using a CDMA algorithm and the abnormality detection circuit is phase locked to the test signal.

20. The electrosurgical generator according to claim 1, wherein the test signal is modulated using a maximum length sequence (MLS) algorithm.

* * * * *